(12) United States Patent
Du et al.

(10) Patent No.: US 10,421,723 B2
(45) Date of Patent: Sep. 24, 2019

(54) 2,3-DIACYLATED, 2- AND 3-MONO-ACYLATED ALKYLATED IMINO SUGARS EXHIBITING GLUCOSIDASE INHIBITION AND THEIR METHOD OF USE

(71) Applicant: Baruch S. Blumberg Institute, Doylestown, PA (US)

(72) Inventors: Yanming Du, Cheshire, CT (US); Jinhong Chang, Chalfont, PA (US); Timothy Michael Block, Doylestown, PA (US)

(73) Assignee: BARUCH S. BLUMBERG INSTITUTE

( * ) Notice: Subject to any disclaimer, the term of this patent is extended or adjusted under 35 U.S.C. 154(b) by 0 days.

(21) Appl. No.: 15/492,652

(22) Filed: Apr. 20, 2017

(65) Prior Publication Data

US 2017/0305856 A1 Oct. 26, 2017

Related U.S. Application Data

(60) Provisional application No. 62/325,018, filed on Apr. 20, 2016.

(51) Int. Cl.
| | | |
|---|---|---|
| C07D 211/40 | (2006.01) | |
| C07D 211/36 | (2006.01) | |
| C07D 419/12 | (2006.01) | |
| A61K 31/45 | (2006.01) | |
| A61K 31/13 | (2006.01) | |

(52) U.S. Cl.
CPC ............ C07D 211/40 (2013.01); A61K 31/13 (2013.01); A61K 31/45 (2013.01); C07D 211/36 (2013.01); C07D 419/12 (2013.01)

(58) Field of Classification Search
CPC .. C07D 211/40; C07D 211/36; C07D 419/12; A61K 31/13; A61K 31/45
See application file for complete search history.

(56) References Cited

FOREIGN PATENT DOCUMENTS

WO    WO-2013148791 A1 * 10/2013  ........... C07D 207/12

OTHER PUBLICATIONS

Delinck et al., Tetrahedron Lett., 1990, 31(22), p. 3093-3096. (Year: 1990).*
Wuts et al., Greene's Protective Groups in Organic Synthesis, 4th ed., 2007, John Wiley & Sons, Inc., p. 1-366. (Year: 2007).*

* cited by examiner

Primary Examiner — Jonathan S Lau
(74) Attorney, Agent, or Firm — The Belles Group, P.C.

(57) ABSTRACT

Described herein are alkylated imino sugars derivatives having a disease-modifying action in the treatment of diseases associated with glucosidase activity that include viral hemorrhagic fevers and other enveloped viruses, and any other diseases involving glucosidase activity.

20 Claims, No Drawings

2,3-DIACYLATED, 2- AND 3-MONO-ACYLATED ALKYLATED IMINO SUGARS EXHIBITING GLUCOSIDASE INHIBITION AND THEIR METHOD OF USE

CROSS-REFERENCE TO RELATED APPLICATION

This application claims the benefit of priority from U.S. Provisional Application No. 62/325,018, filed Apr. 20, 2016, entitled: "Novel Diacylated and Mono-acylated Alkylated Imino Sugars Exhibiting Glucosidase Inhibition and Their Method of Use", the contents of which are hereby incorporated herein in their entirety.

STATEMENT REGARDING FEDERALLY SPONSORED RESEARCH

The inventions described herein were made, in part, with support from Grant No. R01A1104636 awarded by the National Institute of Health (NIH). As such, the United States government may have certain rights to the inventions described herein.

FIELD OF THE DISCLOSURE

The present invention pertains to Deoxynojirimycin (DNJ) imino sugar compounds and their use as agents for treating viral hemorrhagic fevers and related conditions. These compounds are useful as glucosidase inhibitors. The present invention provides novel chemical compounds, and the use of these compounds alone or in combination with other antiviral agents for the treatment of viral infection and other diseases that involve glucosidase activity.

BACKGROUND

Viral hemorrhagic fevers (VHFs) refer to severe multisystem syndrome, caused by viruses of four distinct families: arenaviruses, filoviruses, bunyaviruses, and flaviviruses. These symptoms are often accompanied by hemorrhage (bleeding). While some types of hemorrhagic fever viruses can cause relatively mild illnesses, many of these viruses cause severe, life-threatening disease. Currently, there is limited treatment or established cure for VHF infection. Ribavirin, an antiviral drug, has been effective in treating some individuals with Lassa fever or hemorrhagic fever with renal syndrome (HFRS). Treatment with convalescent-phase plasma has been used with success in some patients with Argentine hemorrhagic fever. There is a dengue vaccine, Dengvaxia®, has been approved for use in several countries, but its coverage is not complete: it is more effective for individuals 9-45 years of age, and has higher against serotypes 3 and 4 (71.6% and 76.9%, respectively) than for serotypes 1 and 2 (54.7% and 43.0%) based on the phase clinical trials.

The Ebola Outbreak in West Africa of 2014 is the largest one in history, As of Mar. 24, 2016: Laboratory-Confirmed Cases: 15,253, Total Deaths: 11,320 (74%). There are no effective medical treatments for managing Filovirus infection (Jinhong 2014). The pipeline for candidate Filovirus therapeutics is limited, but recent promising work with novel nucleotide prodrug GS-5734 (Warren et al 2016), nucleoside BCX-4430 (Biocryst Pharmaceuticals), entry inhibitors (Cote et al., 2011), post entry, s-adenosine homocystein hydrolase (SAHS) inhibitors (Huggins, Zhang, and Bray, 1999), antisense oligo (Warren et al., 2010b), immuno-adhesion (Radoshitzky et al., 2011), and chimeric monoclonal ZMapp approaches have been reported. It is unclear which, if any, of these approaches will become clinically developed; all are in very early or clinical stages. The imino sugars with known target (host ER □-glucosidases) and would be complementary to these approaches, and have the advantage of being broadly active.

Our approach to developing antiviral compounds is to design a molecule targeting host factors that are essential for the virus life cycle, thereby providing antiviral effect. In theory, by targeting host pathways used in common by all the hemorrhagic fever viruses, it should be possible to discover broad spectrum antiviral agents. If the viruses are more dependent upon the host pathway than is the host, selectivity and a useful therapeutic is possible. Viral hemorrhagic fevers (VHF) viruses each contain different RNA genomes, but they are all enveloped with glycosylated viral proteins and share a similar morphogenesis strategy of budding, which would make them sensitive to glucosidase inhibitors. This is presumably because the folding of N-linked glycoproteins in these viruses depends upon calnexin, a chaperon that folds proteins that have been trimmed by the Endoplasmic reticulum (ER) glucosidase. Most cell functions can compensate for a reduction in glucosidase enzyme function; however, the calnexin dependent viral envelope proteins cannot apparently use alternative processing pathways. Thus, glucosidase inhibitors would be selective antiviral agents against multiple enveloped viruses.

Imino sugars, such as deoxynojirimycin (DNJ) and its derivatives have been found glucosidase inhibitors. Despite great potential as broad-spectrum antivirals, clinical development of imino sugars has been limited by their low efficacy. The glucosidase inhibitors, N-butyl-DNJ (NBDNJ) currently approved by the US and European FDAs for use in the management of Gaucher's disease and Celgosivir (in Phase II human trials for Hepatitis C virus infection), both require near millimolar concentrations to achieve $EC_{50}$ values in tissue culture against their target viruses. NBDNJ has been dropped for antiviral development, due to the failure to achieve therapeutic concentration in vivo. Several more potent DNJ derivatives have been prepared with submicro molar $EC_{50}$ (Chang et al, 2014), but the urgent and unmet need to identify agents with broad virus coverage supports the need for continuing efforts to seek novel and more effective glucosidase inhibitors useful as antiviral agents.

Success of imino sugars as human used antiviral agents, which has in the past required constitutive high serum concentrations of drug, has been, to some extent, limited by the GI distress (diarrhea) (Butters, 2007; Durantel, 2009) caused by inhibition of intestinal glucosidases (Reuser and Wisselaar, 1994). Unlike imino sugar's antiviral target, intracellular ER □-glucosidases, these intestinal glucosidases are in the brush border of the small intestines with their active site facing the lumen. Therefore, side effects occur following oral administration (Reuser and Wisselaar, 1994), and are unrelated to antiviral efficacy (Jacob and Bryant, 1993).

Also limiting the utility of imino sugars as viable therapeutic agents is their sometimes poor pharmacokinetic properties, as shown by their high efflux ratios (Jinhong, 2013). These poor properties can limit the intestinal absorption of an agent and limit uptake into the target tissue or cell. To improve on their properties prodrugs of imino sugars have been employed. It has been demonstrated that preparation of imino sugar pan-esters improves the systemic absorption of an imino sugar (Cook, C. S.; et al. Pharmaceutical Research, 1995, 12, 1158-1164) and furthermore, the ester moiety of these "prosugars" is masked with neutral lipophilic groups to obtain a suitable partition coefficient to optimize uptake and transport into the cell dramatically enhancing the intracellular concentration of the imno sugar analog relative to administering the parent imno sugars alone (P. S. Sunkara, D. L. Taylor, M. S. Kang, T. L. Bowlin, P. S. Liu, A. S. Tyms and A. Sjoerdsma, Lancet, 1989, I, 1206).

The present invention addresses the need for new antiviral drugs that are both disease-modifying and effective in treating patients that are infected with viral hemorrhagic fever (VHFs) viruses. The present invention also addresses the long felt need for new treatments for and means of preventing diseases that involve viral infection and other diseases that involve glucosidase activity.

SUMMARY

The present invention is directed toward novel alkylated imino sugars, compounds of formula (I),

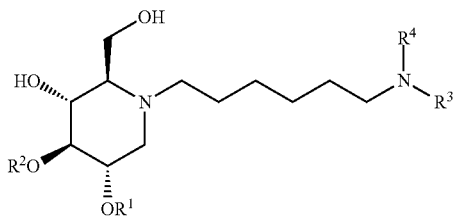

(I)

Including hydrates, solvates, pharmaceutically acceptable salts, prodrugs and complexes thereof, wherein:

$R^1$ at each occurrence is independently selected from the group consisting of hydrogen and $COR^5$;

$R^2$ at each occurrence is independently selected from the group consisting of hydrogen and $COR^5$;

$R^3$ is selected from a group consisting of hydrogen, optionally substituted $C_{1-6}$ alkyl, optionally substituted $C_{3-14}$ cycloalkyl, $COR^6$, $CO_2R^7$, $SO_2R^8$, $CONHR^9$, and $P(O)(OR^{10})_2$;

$R^4$ is selected from a group consisting of hydrogen, optionally substituted $C_{1-6}$ alkyl, optionally substituted $C_{3-14}$ cycloalkyl, 1-adamantyl, 2-adamantyl, and optionally substituted aryl which may be substituted by 0-5 moieties;

$R^4$ and $R^7$ are taken together with the atom to which they are bound to form an optionally substituted ring having 5 ring atoms;

$R^4$ and $R^7$ are taken together with the atom to which they are bound to form

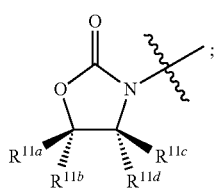

$R^4$ and $R^7$ are taken together with the atom to which they are bound to form

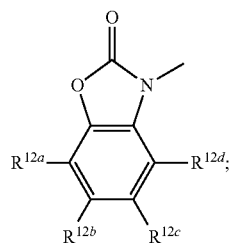

$R^5$ at each occurrence is independently selected from the group consisting of optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties, $OR^{13}$,

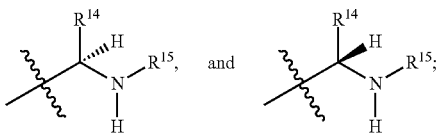

When $R^1$ is hydrogen, $R^2$ is not hydrogen;
When $R^1$ is hydrogen, $R^5$ is not optionally substituted $C_{1-6}$ alkyl;
When $R^1$ is hydrogen, $R^5$ is not optionally substituted branched $C_{1-6}$ alkyl;
When $R^2$ is hydrogen, $R^5$ is not optionally substituted $C_{1-6}$ alkyl;
When $R^2$ is hydrogen, $R^5$ is not optionally substituted branched $C_{1-6}$ alkyl;
No more than one $R^5$ may be optionally substituted $C_{1-6}$ alkyl;
No more than on $R^5$ may be optionally substituted branched $C_{1-6}$ alkyl;
$R^6$ is selected from a group consisting of an optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;
$R^7$ is selected from a group consisting of an optionally substituted $C_{1-10}$ alkyl, optionally substituted $C_{3-14}$ cycloalkyl, and optionally substituted branched $C_{1-6}$ alkyl;
$R^8$ is selected from a group consisting of optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;
$R^9$ is selected from a group consisting of hydrogen, optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;
$R^{10}$ is selected from a group consisting of optionally substituted $C_{1-10}$ alkyl, optionally substituted branched $C_{3-10}$ alkyl and optionally substituted cyclic $C_{3-14}$ cycloalkyl;
$R^{11a}$, $R^{11b}$, $R^{11c}$, and $R^{11d}$ are each independently selected from a group consisting of hydrogen, optionally substituted $C_{1-6}$ alkyl, and optionally substituted aryl which may be substituted by 0-5 moieties;
$R^{12a}$, $R^{12b}$, $R^{12c}$, and $R^{12d}$ are each independently selected from a group consisting of hydrogen, halogen, optionally substituted $C_{1-6}$ alkyl, optionally substituted branched $C_{1-6}$ alkyl, and optionally substituted $C_{1-6}$ alkoxy;
$R^{13}$ is independently selected at each occurrence from a group consisting of optionally substituted $C_{1-10}$ alkyl, optionally substituted branched $C_{1-10}$ alkyl, optionally substituted $C_{3-8}$ cycloalkyl, and optionally substituted aryl which may be substituted by 0-5 moieties;

$R^{14}$ is selected from a group consisting of optionally substituted $C_{1-10}$ alkyl, optionally substituted branched $C_{1-10}$ alkyl, optionally substituted $C_{3-14}$ cycloalkyl, optionally substituted aryl which may be substituted by 0-5 moieties, optionally substituted benzyl which may be substituted by 0-5 moieties, —CH2OR$^{16}$, CH(CH3)OR$^{16}$, CH$_2$SR$^{16}$, CH$_2$CH$_2$SCH$_3$, CH$_2$CH$_2$CH$_2$CH$_2$NR$^{17a}$R$^{17b}$, CH$_2$COR$^{18}$, CH$_2$CH$_2$COR$^{18}$,

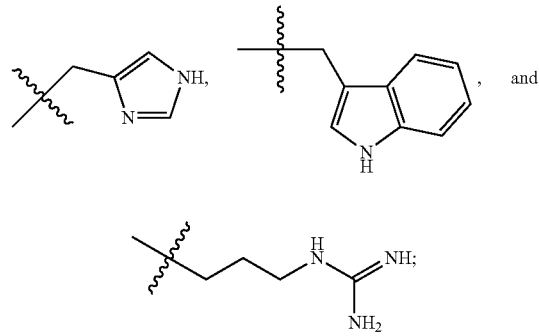

and

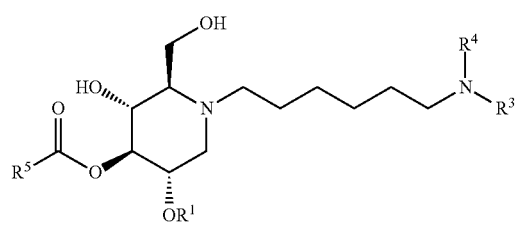

$R^{15}$ is selected from a group consisting of COR$^6$, CO$_2$R$^7$, SO$_2$R$^8$, CONHR$^9$, and P(O)(OR$^{10}$)$_2$;

$R^{16}$ is selected from the group consisting of hydrogen, optionally substituted $C_{1-10}$ alkyl, and optionally substituted branched $C_{1-10}$ alkyl;

$R^{17a}$ is selected from the group consisting of hydrogen, optionally substituted $C_{1-10}$ alkyl, and optionally substituted branched $C_{1-10}$ alkyl;

$R^{17b}$ is selected from the group consisting of hydrogen, optionally substituted $C_{1-10}$ alkyl, and optionally substituted branched $C_{1-10}$ alkyl;

$R^{18}$ is selected from the group consisting of OH, NH$_2$, and $C_{1-6}$ alkoxy.

The compounds of the present invention include compounds having formula (II):

(II)

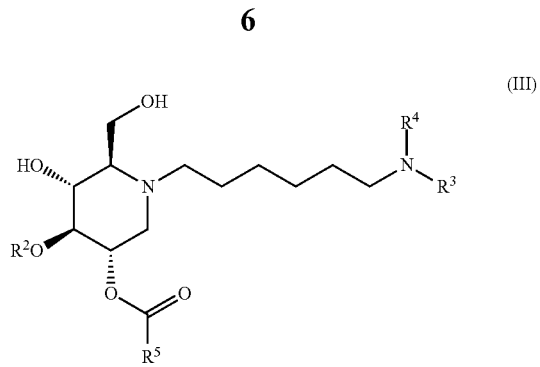

including hydrates, solvates, pharmaceutically acceptable salts, and complexes thereof.

The compounds of the present invention include compounds having formula (III):

(III)

including hydrates, solvates, pharmaceutically acceptable salts, and complexes thereof.

The compounds of the present invention include compounds having formula (IV):

(IV)

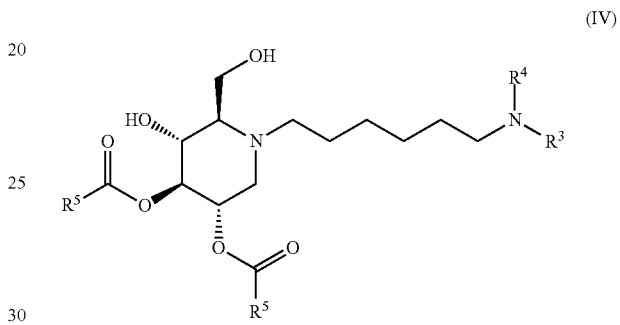

including hydrates, solvates, pharmaceutically acceptable salts, and complexes thereof.

The compounds of the present invention include compounds having formula (V):

(V)

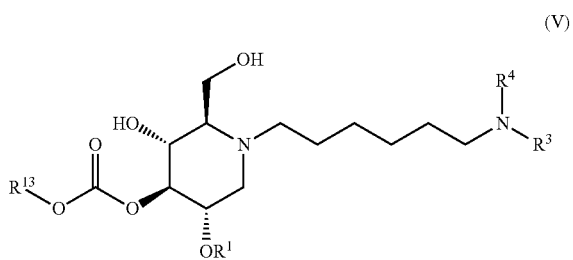

including hydrates, solvates, pharmaceutically acceptable salts, and complexes thereof.

The compounds of the present invention include compounds having formula (VI):

(VI)

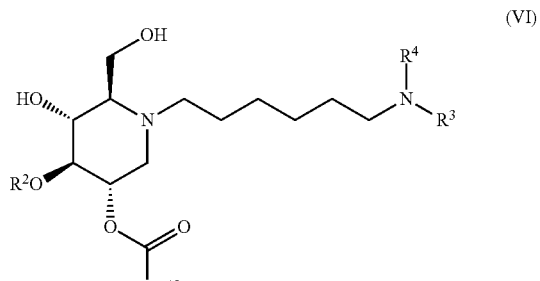

including hydrates, solvates, pharmaceutically acceptable salts, and complexes thereof.

The compounds of the present invention include compounds having formula (VII):

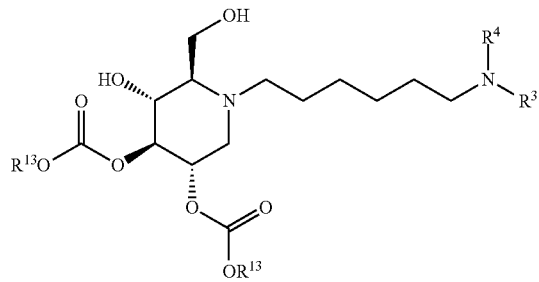
(VII)

including hydrates, solvates, pharmaceutically acceptable salts, and complexes thereof.

The compounds of the present invention include compounds having formula (VIII):

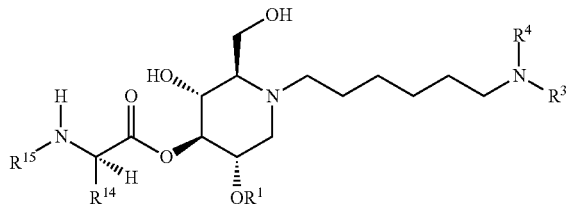
(VIII)

including hydrates, solvates, pharmaceutically acceptable salts, and complexes thereof.

The compounds of the present invention include compounds having formula (IX):

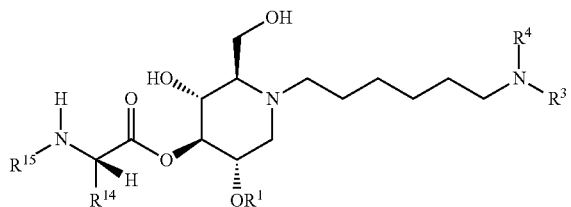
(IX)

including hydrates, solvates, pharmaceutically acceptable salts, and complexes thereof.

The compounds of the present invention include compounds having formula (X):

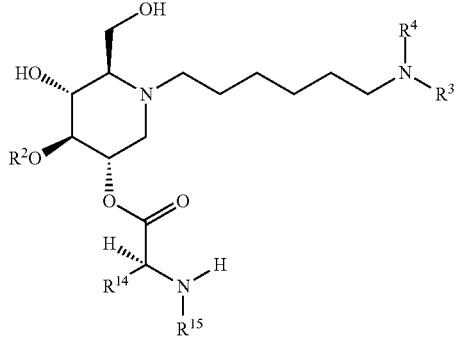
(X)

including hydrates, solvates, pharmaceutically acceptable salts, and complexes thereof.

The compounds of the present invention include compounds having formula (XI):

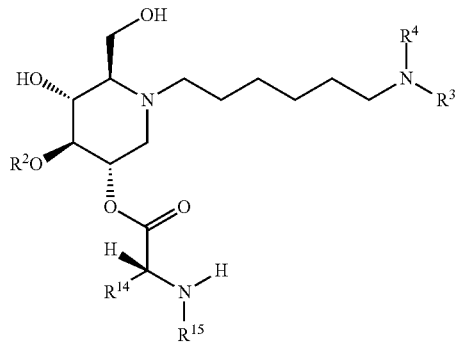
(XI)

including hydrates, solvates, pharmaceutically acceptable salts, and complexes thereof.

The compounds of the present invention include compounds having formula (XII):

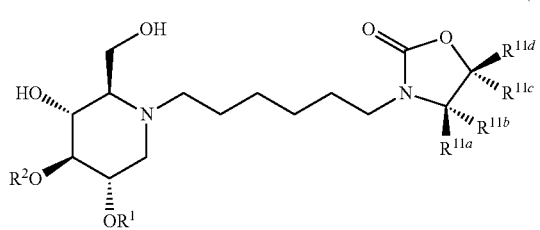
(XII)

including hydrates, solvates, pharmaceutically acceptable salts, and complexes thereof.

The compounds of the present invention include compounds having formula (XIII):

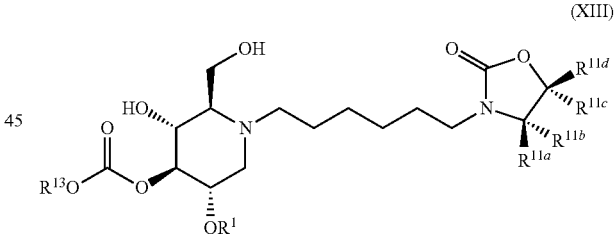
(XIII)

including hydrates, solvates, pharmaceutically acceptable salts, and complexes thereof.

The compounds of the present invention include compounds having formula (XIV):

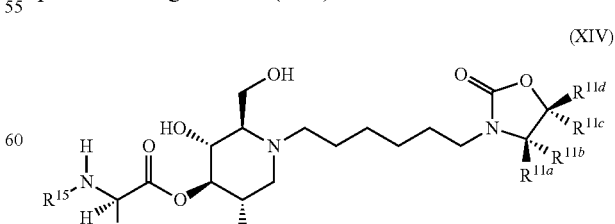
(XIV)

including hydrates, solvates, pharmaceutically acceptable salts, and complexes thereof.

The compounds of the present invention include compounds having formula (XV):

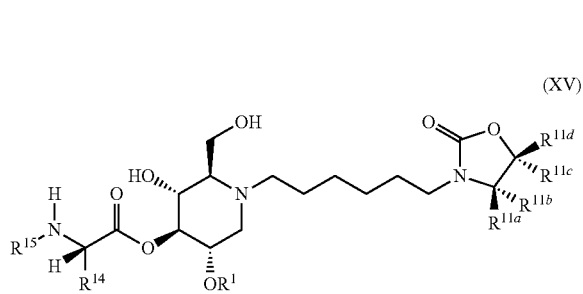

(XV)

including hydrates, solvates, pharmaceutically acceptable salts, and complexes thereof.

The compounds of the present invention include compounds having formula (XVI):

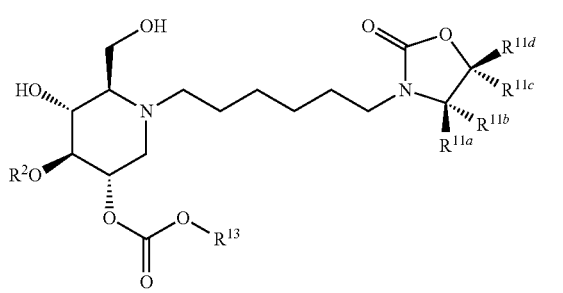

(XVI)

including hydrates, solvates, pharmaceutically acceptable salts, and complexes thereof.

The compounds of the present invention include compounds having formula (XVII):

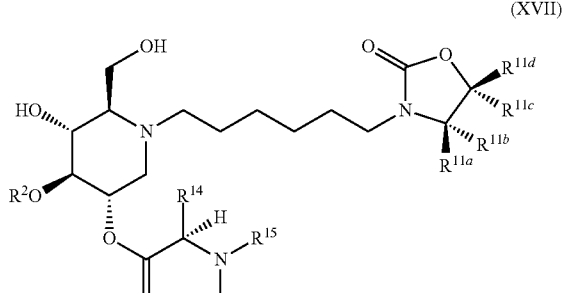

(XVII)

including hydrates, solvates, pharmaceutically acceptable salts, and complexes thereof.

The compounds of the present invention include compounds having formula (XVIII):

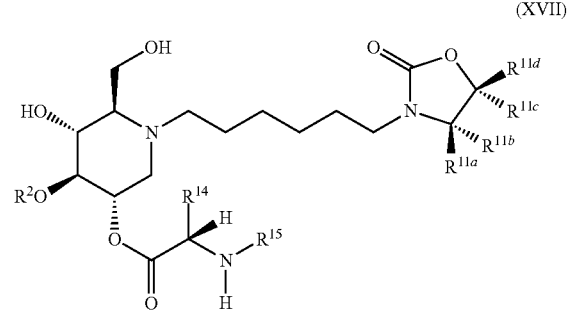

(XVIII)

including hydrates, solvates, pharmaceutically acceptable salts, and complexes thereof.

The compounds of the present invention include compounds having formula (XIX):

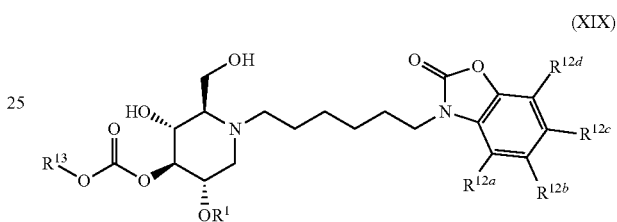

(XIX)

including hydrates, solvates, pharmaceutically acceptable salts, and complexes thereof.

The compounds of the present invention include compounds having formula (XX):

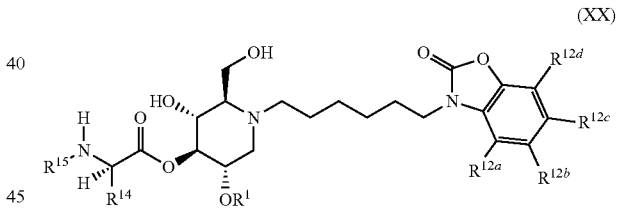

(XX)

including hydrates, solvates, pharmaceutically acceptable salts, and complexes thereof.

The compounds of the present invention include compounds having formula (XXI):

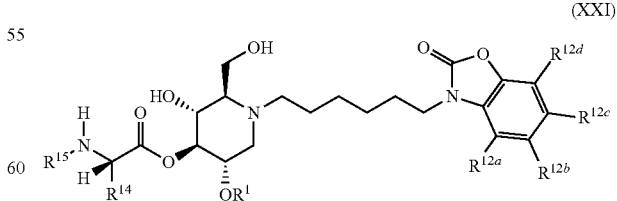

(XXI)

including hydrates, solvates, pharmaceutically acceptable salts, and complexes thereof.

The compounds of the present invention include compounds having formula (XXII):

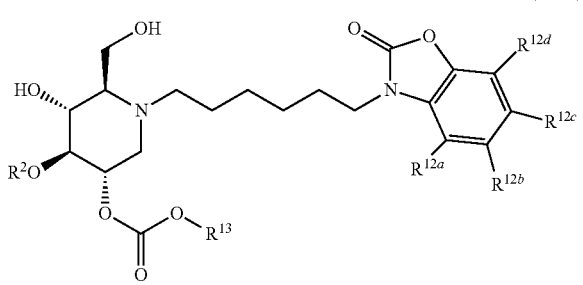

(XXII)

including hydrates, solvates, pharmaceutically acceptable salts, and complexes thereof.

The compounds of the present invention include compounds having formula (XXIII):

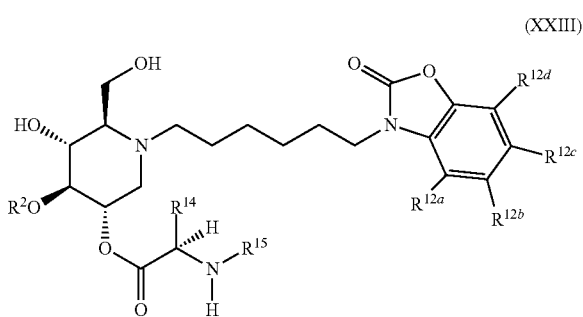

(XXIII)

including hydrates, solvates, pharmaceutically acceptable salts, and complexes thereof.

The compounds of the present invention include compounds having formula (XXIV):

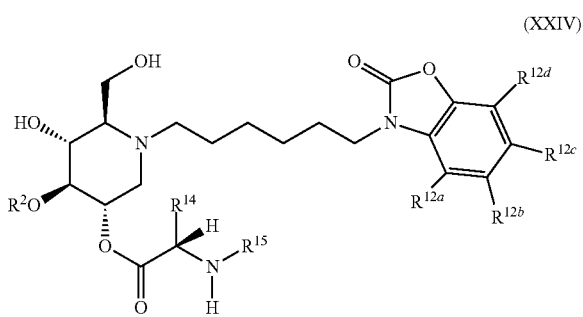

(XXIV)

including hydrates, solvates, pharmaceutically acceptable salts, and complexes thereof.

The present invention further relates to compositions comprising an effective amount of one or more compounds according to the present invention and an excipient.

The present invention also relates to a method for treating or preventing diseases that involve infection with viral hemorrhagic fever (VHFs) viruses, including, for example, infection with arenaviruses, filoviruses, bunyaviruses, and flaviviruses, said method comprising administering to a subject an effective amount of a compound or composition according to the present invention.

The present invention yet further relates to a method for treating or preventing diseases that involve infection with viral hemorrhagic fever (VHFs) viruses, including, for example, infection with arenaviruses, filoviruses, bunyaviruses, and flaviviruses, wherein said method comprises administering to a subject a composition comprising an effective amount of one or more compounds according to the present invention and an excipient.

The present invention also relates to a method for treating or preventing disease or conditions associated with infection with arenaviruses, filoviruses, bunyaviruses, and flaviviruses, and diseases that involve infection with viral hemorrhagic fever (VHFs) viruses. Said methods comprise administering to a subject an effective amount of a compound or composition according to the present invention.

The present invention yet further relates to a method for treating or preventing disease or conditions associated with infection with arenaviruses, filoviruses, bunyaviruses, and flaviviruses, and diseases that involve infection with viral hemorrhagic fever (VHFs) viruses, wherein said method comprises administering to a subject a composition comprising an effective amount of one or more compounds according to the present invention and an excipient.

The present invention also relates to a method for treating or preventing disease or conditions associated with infection with viral hemorrhagic fever (VHFs) viruses. Said methods comprise administering to a subject an effective amount of a compound or composition according to the present invention.

The present invention yet further relates to a method for treating or preventing disease or conditions associated with infection with viral hemorrhagic fever (VHFs) viruses, wherein said method comprises administering to a subject a composition comprising an effective amount of one or more compounds according to the present invention and an excipient.

The present invention further relates to a process for preparing the glucosidase inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION

The glucosidase inhibitors of the present invention are capable of treating and preventing diseases associated with infection with viral hemorrhagic fever (VHFs) viruses, for example infection with arenaviruses, filoviruses, bunyaviruses, and flaviviruses. It has been discovered that viral hemorrhagic fevers (VHF) viruses are enveloped with glycosylated viral proteins and share a similar morphogenesis strategy of budding, making them sensitive to glucosidase inhibitors. This is presumably because the folding of N-linked glycoproteins in these viruses depends upon calnexin, a chaperon that folds proteins that have been trimmed by the ER glucosidase. Most cell functions can compensate for a reduction in glucosidase enzyme function; however, the calnexin dependent viral envelope proteins cannot use alternative processing pathways. Thus, glucosidase inhibitors would be useful as selective antiviral agents against multiple enveloped viruses such as viral hemorrhagic fever (VHFs) viruses, for example arenaviruses, filoviruses, bunyaviruses, and flaviviruses, as well as other enveloped human viruses, for example influenza virus. Without wishing to be limited by theory, it is believed that glucosidase inhibitors of the present invention can ameliorate, abate, otherwise cause to be controlled, diseases associated with infection with viral hemorrhagic fever (VHFs) viruses and other enveloped viruses. Further, without wishing to be limited by theory, it is believed that the novel alkylated imino sugars of the present invention are useful as broad-spectrum antiviral agents.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tent-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl [2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tent-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3 a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

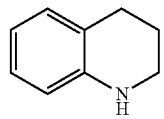

is, for the purposes of the present invention, considered a heterocyclic unit. 6,7-Dihydro-5H-cyclopentapyrimidine having the formula:

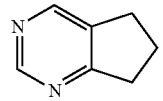

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

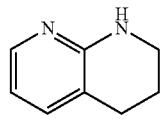

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10)

substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{19}$, —SR$^{19}$, —N(R$^{19}$)$_2$, —NR$^{19}$C(O)R$^{19}$, —SO$_2$R$^{19}$, —SO$_2$OR$^{19}$, —SO$_2$N(R$^{19}$)$_2$, —C(O)R$^{19}$, —C(O)OR$^{19}$, —C(O)N(R$^{19}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{19}$; wherein R$^{19}$, at each occurrence, independently is hydrogen, —OR$^{20}$, —R$^{20}$, —C(O)R$^{20}$, —C(O)OR$^{20}$, —C(O)N(R$^{20}$)$_2$, —SO$_2$R$^{20}$, —S(O)$_2$OR$^{20}$, —N(R$^{20}$)$_2$, —NR$^{20}$C(O)R$^{20}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{19}$ units taken together with the atom(s) to which they are bound form an optionally substituted carbocycle or heterocycle wherein said carbocycle or heterocycle has 3 to 7 ring atoms; wherein R$^{20}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{20}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{21}$; for example, —OH, —OCH$_3$, —OCH$_2$CH$_3$, —OCH$_2$CH$_2$CH$_3$;
ii) —C(O)R$^{21}$; for example, —COCH$_3$, —COCH$_2$CH$_3$, —COCH$_2$CH$_2$CH$_3$;
iii) —C(O)OR$^{21}$; for example, —CO$_2$CH$_3$, —CO$_2$CH$_2$CH$_3$, —CO$_2$CH$_2$CH$_2$CH$_3$;
iv) —C(O)N(R$^{21}$)$_2$; for example, —CONH$_2$, —CONHCH$_3$, —CON(CH$_3$)$_2$;
v) —N(R$^{21}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{21}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{21}$)C(O)R$^{21}$;
xiii) Oxo (=O);
xiv) Heterocycle; and
xv) Heteroaryl.
wherein each R$^{21}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^{21}$ units can be taken together to form a ring comprising 3-7 ring atoms. In certain aspects, each R$^{21}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "Ci-6 alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the glucosidase inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{13})_2$, each $R^{13}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Glucosidase Inhibitors

The glucosidase inhibitors of the present invention are alkylated imino sugars, and include all enantiomeric and diastereomeric forms and pharmaceutically accepted salts thereof having the formula (I):

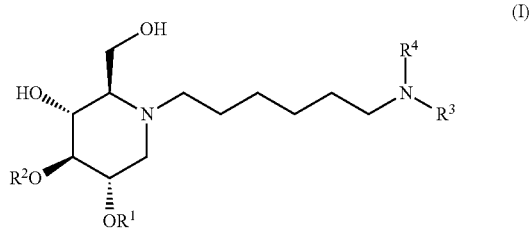

(I)

including hydrates, solvates, pharmaceutically acceptable salts, prodrugs and complexes thereof, wherein:

$R^1$ at each occurrence is independently selected from the group consisting of hydrogen and $COR^5$;

$R^2$ at each occurrence is independently selected from the group consisting of hydrogen and $COR^5$;

$R^3$ is selected from a group consisting of hydrogen, optionally substituted $C_{1-6}$ alkyl, optionally substituted $C_{3-14}$ cycloalkyl, $COR^6$, $CO_2R^7$, $SO_2R^8$, $CONHR^9$, and $P(O)(OR^{10})_2$;

$R^4$ is selected from a group consisting of hydrogen, optionally substituted $C_{1-6}$ alkyl, optionally substituted $C_{3-14}$ cycloalkyl, 1-adamantyl, 2-adamantyl, and optionally substituted aryl which may be substituted by 0-5 moieties;

$R^4$ and $R^7$ are taken together with the atom to which they are bound to form an optionally substituted ring having 5 ring atoms;

$R^4$ and $R^7$ are taken together with the atom to which they are bound to form

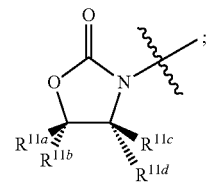

$R^4$ and $R^7$ are taken together with the atom to which they are bound to form

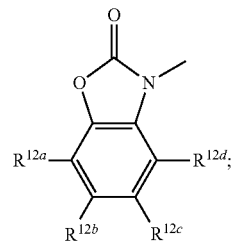

$R^5$ at each occurrence is independently selected from the group consisting of optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties, $OR^{13}$,

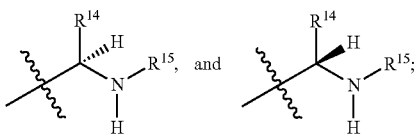

when $R^1$ is hydrogen, $R^2$ is not hydrogen;
when $R^1$ is hydrogen, $R^5$ is not optionally substituted $C_{1-6}$ alkyl;
when $R^1$ is hydrogen, $R^5$ is not optionally substituted branched $C_{1-6}$ alkyl;
when $R^2$ is hydrogen, $R^5$ is not optionally substituted $C_{1-6}$ alkyl;
when $R^2$ is hydrogen, $R^5$ is not optionally substituted branched $C_{1-6}$ alkyl;

no more than one $R^5$ may be optionally substituted $C_{1-6}$ alkyl;

no more than on $R^5$ may be optionally substituted branched $C_{1-6}$ alkyl;

$R^6$ is selected from a group consisting of an optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^7$ is selected from a group consisting of an optionally substituted $C_{1-10}$ alkyl, optionally substituted $C_{3-14}$ cycloalkyl, and optionally substituted branched $C_{1-6}$ alkyl;

$R^8$ is selected from a group consisting of optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^9$ is selected from a group consisting of hydrogen, optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^{10}$ is selected from a group consisting of optionally substituted $C_{1-10}$ alkyl, optionally substituted branched $C_{3-10}$, and optionally substituted cyclic $C_{3-14}$ cycloalkyl;

$R^{11a}$, $R^{11b}$, $R^{11c}$, and $R^{11d}$ are each independently selected from a group consisting of hydrogen, optionally substituted $C_{1-6}$ alkyl, and optionally substituted aryl which may be substituted by 0-5 moieties;

$R^{12a}$, $R^{12b}$, $R^{12c}$, and $R^{12d}$ are each independently selected from a group consisting of hydrogen, halogen, optionally substituted $C_{1-6}$ alkyl, optionally substituted branched $C_{1-6}$ alkyl, and optionally substituted $C_{1-6}$ alkoxy;

$R^{13}$ is independently selected at each occurrence from a group consisting of optionally substituted $C_{1-10}$ alkyl, optionally substituted branched $C_{1-10}$ alkyl, optionally substituted $C_{3-8}$ cycloalkyl, and optionally substituted aryl which may be substituted by 0-5 moieties;

$R^{14}$ is selected from a group consisting of optionally substituted $C_{1-10}$ alkyl, optionally substituted branched $C_{1-10}$ alkyl, optionally substituted $C_{3-14}$ cycloalkyl, optionally substituted aryl which may be substituted by 0-5 moieties, optionally substituted benzyl which may be substituted by 0-5 moieties, $-CH_2OR^{16}$, $CH(CH_3)OR^{16}$, $CH_2SR^{16}$, $CH_2CH_2SCH_3$, $CH_2CH_2CH_2CH_2NR^{17a}R^{17b}$, $CH_2COR^{18}$, $CH_2CH_2COR^{18}$,

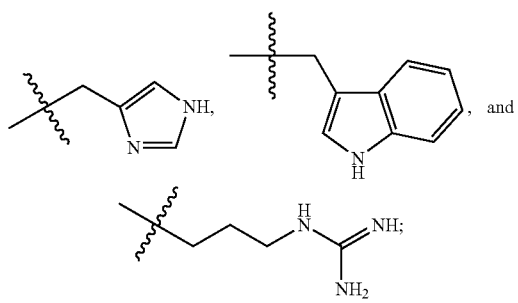

$R^{15}$ is selected from a group consisting of $COR^6$, $CO_2R^7$, $SO_2R^8$, $CONHR^9$, and $P(O)(OR^{10})_2$;

$R^{16}$ is selected from the group consisting of hydrogen, optionally substituted $C_{1-10}$ alkyl, and optionally substituted branched $C_{1-10}$ alkyl;

$R^{17a}$ is selected from the group consisting of hydrogen, optionally substituted $C_{1-10}$ alkyl, and optionally substituted branched $C_{1-10}$ alkyl;

$R^{17b}$ is selected from the group consisting of hydrogen, optionally substituted $C_{1-10}$ alkyl, and optionally substituted branched $C_{1-10}$ alkyl;

$R^{18}$ is selected from the group consisting of OH, $NH_2$, and $C_{1-6}$ alkoxy.

The compounds of the present invention include compounds having formula (II):

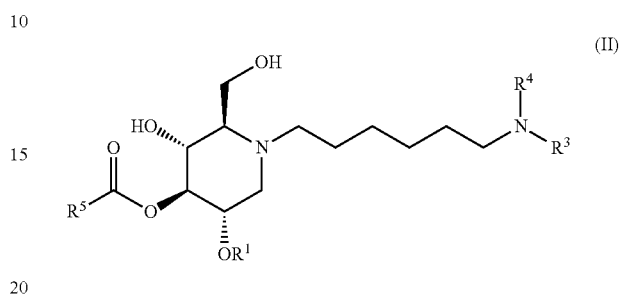

(II)

including hydrates, solvates, pharmaceutically acceptable salts, and complexes thereof.

The compounds of the present invention include compounds having formula (III):

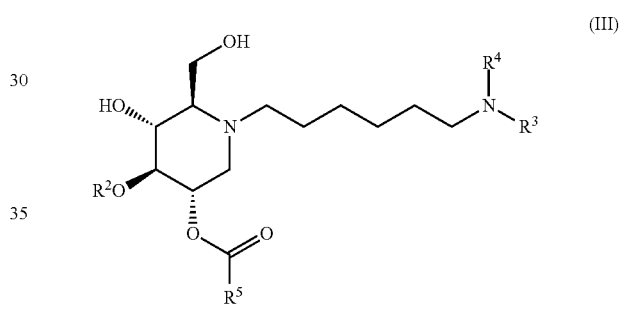

(III)

including hydrates, solvates, pharmaceutically acceptable salts, and complexes thereof.

The compounds of the present invention include compounds having formula (IV):

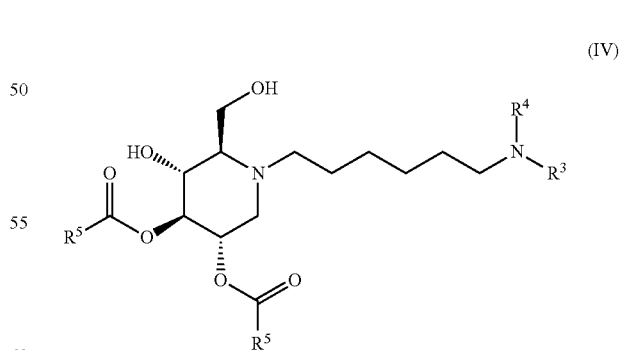

(IV)

including hydrates, solvates, pharmaceutically acceptable salts, and complexes thereof.

The compounds of the present invention include compounds having formula (V):

(V)

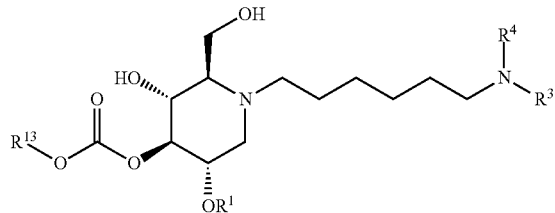

including hydrates, solvates, pharmaceutically acceptable salts, and complexes thereof.

The compounds of the present invention include compounds having formula (VI):

(VI)

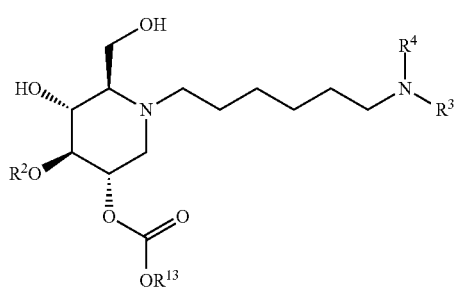

including hydrates, solvates, pharmaceutically acceptable salts, and complexes thereof.

The compounds of the present invention include compounds having formula (VII):

(VII)

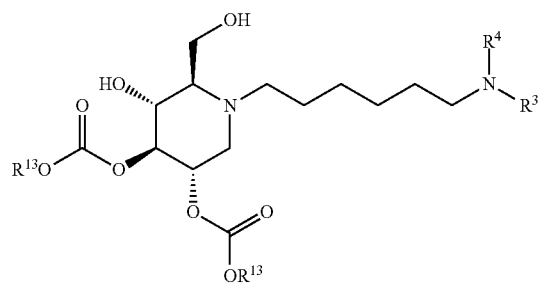

including hydrates, solvates, pharmaceutically acceptable salts, and complexes thereof.

The compounds of the present invention include compounds having formula (VIII):

(VIII)

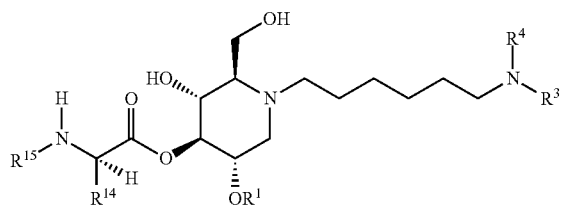

including hydrates, solvates, pharmaceutically acceptable salts, and complexes thereof.

The compounds of the present invention include compounds having formula (IX):

(IX)

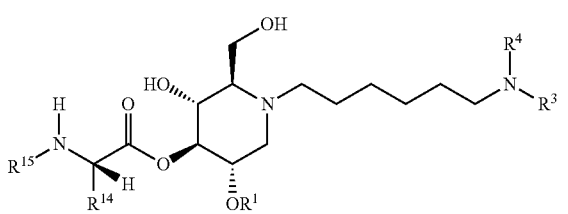

including hydrates, solvates, pharmaceutically acceptable salts, and complexes thereof.

The compounds of the present invention include compounds having formula (X):

(X)

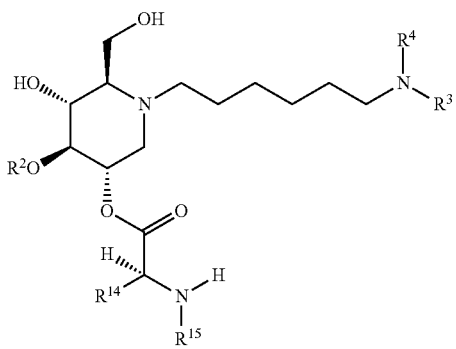

including hydrates, solvates, pharmaceutically acceptable salts, and complexes thereof.

The compounds of the present invention include compounds having formula (XI):

(XI)

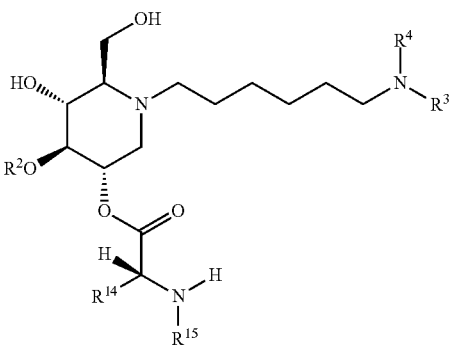

including hydrates, solvates, pharmaceutically acceptable salts, and complexes thereof.

The compounds of the present invention include compounds having formula (XII):

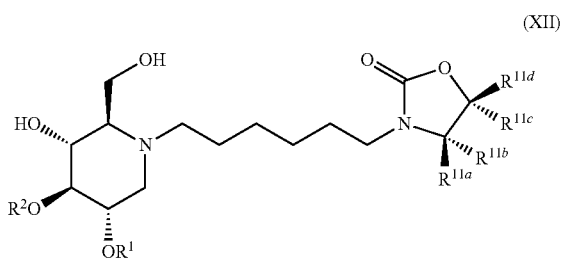

including hydrates, solvates, pharmaceutically acceptable salts, and complexes thereof.

The compounds of the present invention include compounds having formula (XIII):

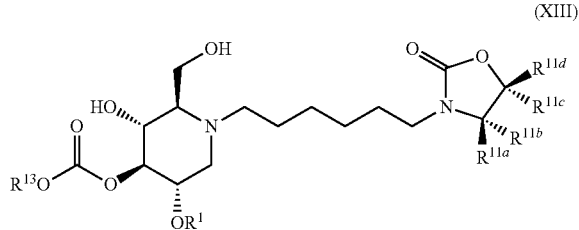

including hydrates, solvates, pharmaceutically acceptable salts, and complexes thereof.

The compounds of the present invention include compounds having formula (XIV):

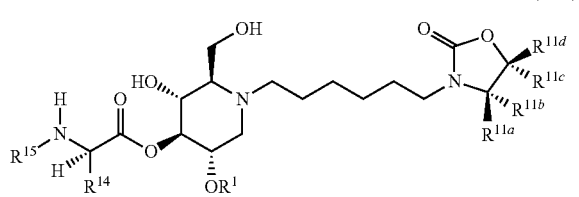

including hydrates, solvates, pharmaceutically acceptable salts, and complexes thereof.

The compounds of the present invention include compounds having formula (XV):

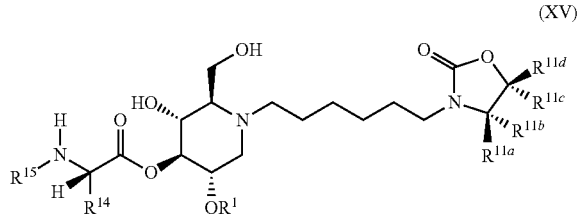

including hydrates, solvates, pharmaceutically acceptable salts, and complexes thereof.

The compounds of the present invention include compounds having formula (XVI):

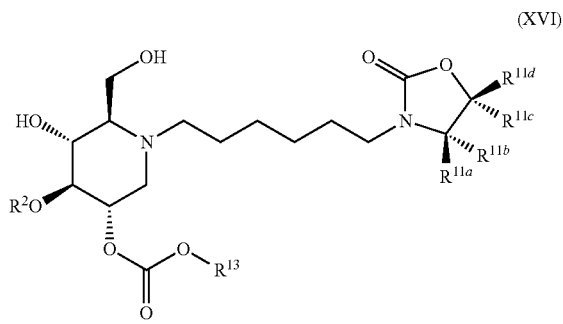

including hydrates, solvates, pharmaceutically acceptable salts, and complexes thereof.

The compounds of the present invention include compounds having formula (XVII):

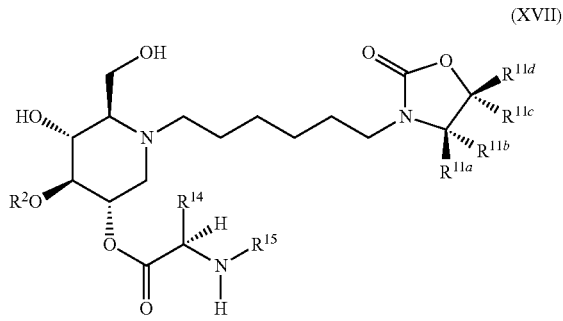

including hydrates, solvates, pharmaceutically acceptable salts, and complexes thereof.

The compounds of the present invention include compounds having formula (XVIII):

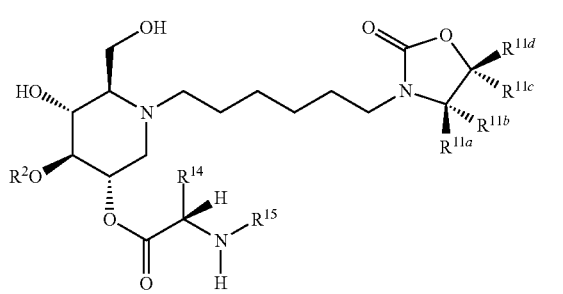

including hydrates, solvates, pharmaceutically acceptable salts, and complexes thereof.

The compounds of the present invention include compounds having formula (XIX):

(XIX)

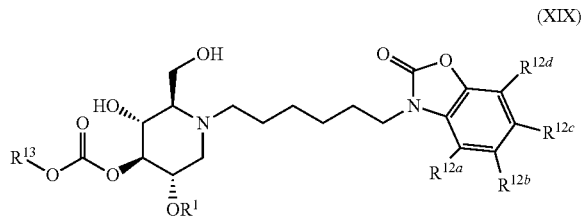

including hydrates, solvates, pharmaceutically acceptable salts, and complexes thereof.

The compounds of the present invention include compounds having formula (XX):

(XX)

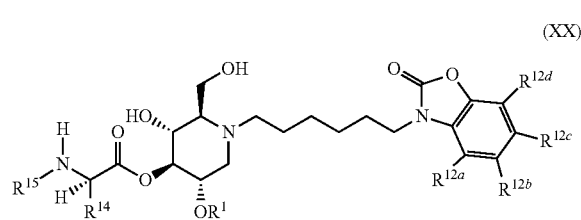

including hydrates, solvates, pharmaceutically acceptable salts, and complexes thereof.

The compounds of the present invention include compounds having formula (XXI):

(XXI)

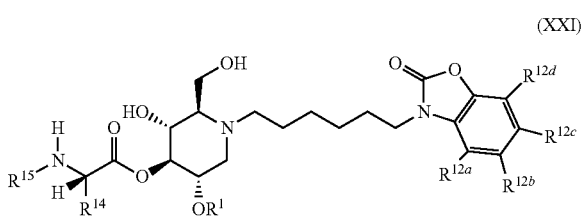

including hydrates, solvates, pharmaceutically acceptable salts, and complexes thereof.

The compounds of the present invention include compounds having formula (XXII):

(XXII)

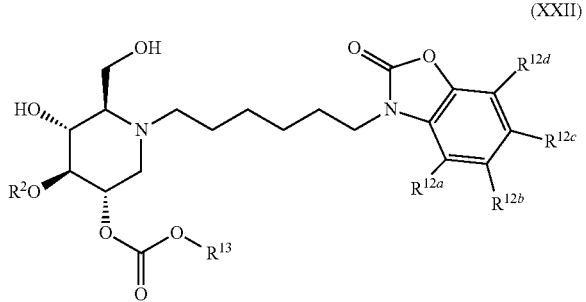

including hydrates, solvates, pharmaceutically acceptable salts, and complexes thereof.

The compounds of the present invention include compounds having formula (XXIII):

(XXIII)

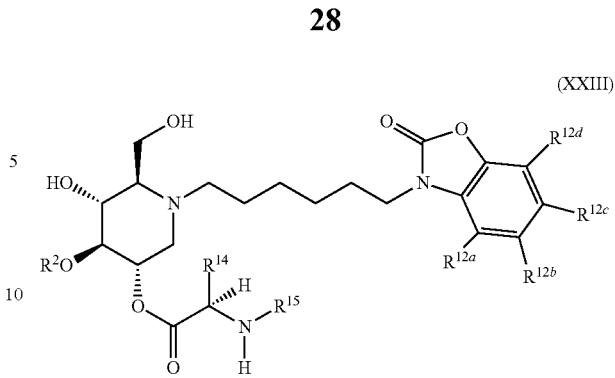

including hydrates, solvates, pharmaceutically acceptable salts, and complexes thereof.

The compounds of the present invention include compounds having formula (XXIV):

(XXIV)

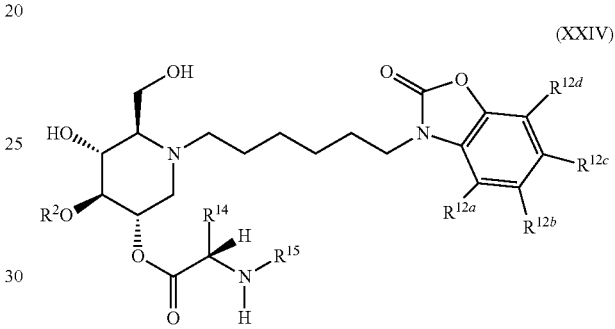

including hydrates, solvates, pharmaceutically acceptable salts, and complexes thereof.

In some embodiments $R^1$ is hydrogen. In some embodiments $R^1$ is $COR^{5a}$.

In some embodiments $R^2$ is hydrogen. In some embodiments $R^2$ is $COR^{5a}$.

In some embodiments $R^3$ is hydrogen. In some embodiments $R^3$ is optionally substituted $C_{1-6}$ alkyl. In some embodiments $R^3$ is optionally substituted $C_{3-14}$ cycloalkyl. In some embodiments $R^3$ is $COR^6$. In some embodiments $R^3$ is $CO_2R^7$. In some embodiments $R^3$ is $SO_2R^8$. In some embodiments $R^3$ is $CONHR^9$. In some embodiments $R^3$ is $P(O)(OR^{10})_2$.

In some embodiments $R^4$ is hydrogen. In some embodiments $R^4$ is optionally substituted $C_{1-6}$ alkyl. In some embodiments $R^4$ is optionally substituted $C_{3-14}$ cycloalkyl. In some embodiments $R^4$ is 1-adamantyl. In some embodiments $R^4$ is 2-adamantyl. In some embodiments $R^4$ is optionally substituted aryl which may be substituted by 0-5 moieties.

In some embodiments $R^4$ and $R^7$ are taken together with the atom to which they are bound to form an optionally substituted ring having 5 ring atoms. In some embodiments $R^4$ and $R^7$ are taken together with the atom to which they are bound to form

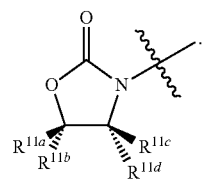

In some embodiments $R^4$ and $R^7$ are taken together with the atom to which they are bound to form

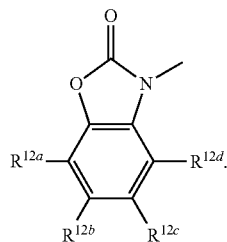

In some embodiments $R^5$ is optionally substituted $C_{1-10}$ alkyl. In some embodiments $R^5$ is optionally substituted branched $C_{1-10}$ alkyl. In some embodiments $R^5$ is optionally substituted $C_{3-14}$ cycloalkyl. In some embodiments $R^5$ is optionally substituted aryl which may be substituted by 0-5 moieties. In some embodiments $R^5$ is $OR^{13}$. In some embodiments $R^5$ is

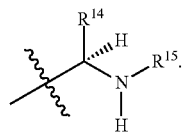

In some embodiments $R^5$ is

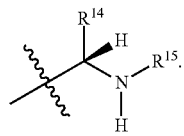

In some embodiments $R^6$ is optionally substituted $C_{1-10}$ alkyl. In some embodiments $R^6$ is optionally substituted branched $C_{1-10}$ alkyl. In some embodiments $R^6$ is optionally substituted $C_{3-14}$ cycloalkyl. In some embodiments $R^6$ is optionally substituted aryl which may be substituted by 0-5 moieties.

In some embodiments $R^7$ is optionally substituted $C_{1-10}$ alkyl. In some embodiments $R^7$ is optionally substituted $C_{3-14}$ cycloalkyl. In some embodiments $R^7$ is optionally substituted branched $C_{1-6}$ alkyl.

In some embodiments $R^8$ is optionally substituted $C_{1-10}$ alkyl. In some embodiments $R^8$ is optionally substituted branched $C_{1-10}$ alkyl. In some embodiments $R^8$ is optionally substituted $C_{3-14}$ cycloalkyl. In some embodiments $R^8$ is optionally substituted aryl which may be substituted by 0-5 moieties.

In some embodiments $R^9$ is hydrogen. In some embodiments $R^9$ is optionally substituted $C_{1-10}$ alkyl. In some embodiments $R^9$ is optionally substituted branched $C_{1-10}$ alkyl. In some embodiments $R^9$ is optionally substituted $C_{3-14}$ cycloalkyl. In some embodiments $R^9$ is optionally substituted aryl which may be substituted by 0-5 moieties.

In some embodiments $R^{10}$ is optionally substituted $C_{1-10}$ alkyl. In some embodiments $R^{10}$ is optionally substituted cyclic $C_{3-14}$ cycloalkyl. In some embodiments $R^{10}$ is optionally substituted branched $C_{3-10}$.

In some embodiments $R^{11a}$ is hydrogen. In some embodiments $R^{11a}$ is optionally substituted $C_{1-6}$ alkyl. In some embodiments $R^{11a}$ is optionally substituted aryl which may be substituted by 0-5 moieties.

In some embodiments $R^{11b}$ is hydrogen. In some embodiments $R^{11b}$ is optionally substituted $C_{1-6}$ alkyl. In some embodiments $R^{11b}$ is optionally substituted aryl which may be substituted by 0-5 moieties.

In some embodiments $R^{11c}$ is hydrogen. In some embodiments $R^{11c}$ is optionally substituted $C_{1-6}$ alkyl. In some embodiments $R^{11c}$ is optionally substituted aryl which may be substituted by 0-5 moieties.

In some embodiments $R^{11d}$ is hydrogen. In some embodiments $R^{11d}$ is optionally substituted $C_{1-6}$ alkyl. In some embodiments $R^{11d}$ is optionally substituted aryl which may be substituted by 0-5 moieties.

In some embodiments $R^{12a}$ is hydrogen. In some embodiments $R^{12a}$ is halogen. In some embodiments $R^{12a}$ is optionally substituted $C_{1-6}$ alkyl. In some embodiments $R^{12a}$ is optionally substituted branched $C_{1-6}$ alkyl. In some embodiments $R^{12a}$ is optionally substituted $C_{1-6}$ alkoxy.

In some embodiments $R^{12b}$ is hydrogen. In some embodiments $R^{12b}$ is halogen. In some embodiments $R^{12b}$ is optionally substituted $C_{1-6}$ alkyl. In some embodiments $R^{12b}$ is optionally substituted branched $C_{1-6}$ alkyl. In some embodiments $R^{12b}$ is optionally substituted $C_{1-6}$ alkoxy.

In some embodiments $R^{12c}$ is hydrogen. In some embodiments $R^{12c}$ is halogen. In some embodiments $R^{12c}$ is optionally substituted $C_{1-6}$ alkyl. In some embodiments $R^{12c}$ is optionally substituted branched $C_{1-6}$ alkyl. In some embodiments $R^{12c}$ is optionally substituted $C_{1-6}$ alkoxy.

In some embodiments $R^{12d}$ is hydrogen. In some embodiments $R^{12d}$ is halogen. In some embodiments $R^{12d}$ is optionally substituted $C_{1-6}$ alkyl. In some embodiments $R^{12d}$ is optionally substituted branched $C_{1-6}$ alkyl. In some embodiments $R^{12d}$ is optionally substituted $C_{1-6}$ alkoxy.

In some embodiments $R^{13}$ is optionally substituted $C_{1-10}$ alkyl. In some embodiments $R^{13}$ is optionally substituted branched $C_{1-10}$ alkyl. In some embodiments $R^{13}$ is optionally substituted $C_{3-8}$ cycloalkyl. [0001] In some embodiments $R^{13}$ is optionally substituted aryl which may be substituted by 0-5 moieties.

In some embodiments $R^{14}$ is optionally substituted $C_{1-10}$ alkyl. In some embodiments $R^{14}$ is optionally substituted branched $C_{1-10}$ alkyl. In some embodiments $R^{14}$ is optionally substituted $C_{3-14}$ cycloalkyl. In some embodiments $R^{14}$ is optionally substituted aryl which may be substituted by 0-5 moieties. In some embodiments $R^{14}$ is optionally substituted benzyl which may be substituted by 0-5 moieties. In some embodiments $R^{14}$ is —$CH_2OR^{16}$. In some embodiments $R^{14}$ is $CH(CH_3)OR^{16}$. In some embodiments $R^{14}$ is $CH_2SR^{16}$. In some embodiments $R^{14}$ is $CH_2CH_2SCH_3$. In some embodiments $R^{14}$ is $CH_2CH_2CH_2CH_2NR^{17a}R^{17b}$. In some embodiments $R^{14}$ is $CH_2COR^{18}$. In some embodiments $R^{14}$ is $CH_2CH_2COR^{18}$. In some embodiments $R^{14}$ is,

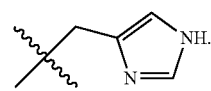

In some embodiments $R^{14}$ is

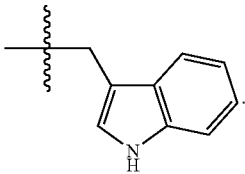 [SMILES: *Cc1c[nH]c2ccccc12]

In some embodiments $R^{14}$ is

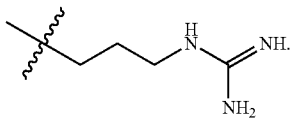 [SMILES: *CCCNC(=N)N]

In some embodiments $R^{15}$ is $COR^6$. In some embodiments $R^{15}$ is $CO_2R^7$. In some embodiments $R^{15}$ is $SO_2R^8$. In some embodiments $R^{15}$ is $CONHR^9$. In some embodiments $R^{15}$ is $P(O)(OR^{10})_2$.

In some embodiments $R^{16}$ is hydrogen. In some embodiments $R^{16}$ is optionally substituted $C_{1-10}$ alkyl. In some embodiments $R^{16}$ is optionally substituted branched $C_{1-10}$ alkyl.

In some embodiments $R^{17a}$ is hydrogen. In some embodiments $R^{17a}$ is, optionally substituted $C_{1-10}$ alkyl. In some embodiments $R^{17a}$ is optionally substituted branched $C_{1-10}$ alkyl.

In some embodiments $R^{17b}$ is hydrogen. In some embodiments $R^{17b}$ is optionally substituted $C_{1-10}$ alkyl. In some embodiments $R^{17b}$ is optionally substituted branched $C_{1-10}$ alkyl.

In some embodiments $R^{18}$ is OH. In some embodiments $R^{18}$ is $NH_2$. In some embodiments $R^{18}$ is $C_{1-6}$ alkoxy.

Other embodiments of the present invention provide A compound having formula (I):

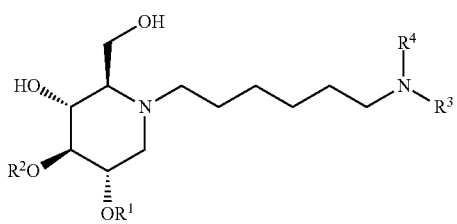

(I)

wherein:

$R^1$ and $R^2$ are independently selected from hydrogen and $COR^5$; and wherein $R^1$ is hydrogen, $R^2$ is not hydrogen;

$R^3$ is selected from hydrogen, optionally substituted $C_{1-6}$ alkyl, optionally substituted $C_{3-14}$ cycloalkyl, $COR^6$, $CO_2R^7$, $SO_2R^8$, $CONHR^9$, and $P(O)(OR^{10})_2$;

$R^4$ is selected from hydrogen, optionally substituted $C_{1-6}$ alkyl, optionally substituted $C_{3-14}$ cycloalkyl, 1-adamantyl, 2-adamantyl, and optionally substituted aryl which may be substituted by 0-5 moieties;

$R^4$ and $R^7$ are taken together with the atom to which they are bound to form an optionally substituted ring having 5 ring atoms;

$R^4$ and $R^7$ are taken together with the atom to which they are bound to form

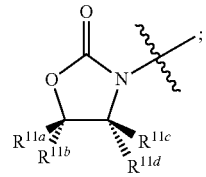

or $R^4$ and $R^7$ are taken together with the atom to which they are bound to form

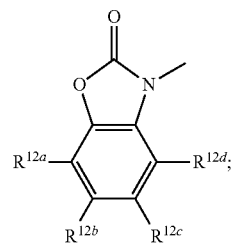

$R^5$ is independently selected from optionally substituted $C_{3-14}$ cycloalkyl, optionally substituted aryl which may be substituted by 0-5 moieties, $OR^{13}$,

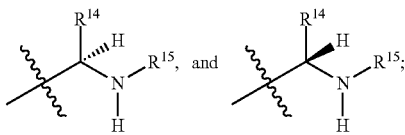

$R^6$ is selected from optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^7$ is selected from optionally substituted $C_{1-10}$ alkyl, optionally substituted $C_{3-14}$ cycloalkyl, and optionally substituted branched $C_{1-6}$ alkyl;

$R^8$ is selected from optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^9$ is selected from hydrogen, optionally substituted $C_{1-10}$ alkyl, optionally substituted branched $C_{1-10}$ alkyl, optionally substituted $C_{3-14}$ cycloalkyl, and optionally substituted aryl which may be substituted by 0-5 moieties;

$R^{10}$ is selected from optionally substituted $C_{1-10}$ alkyl, optionally substituted branched $C_{3-10}$, and optionally substituted cyclic $C_{3-14}$ cycloalkyl;

$R^{11a}$, $R^{11b}$, $R^{11c}$, and $R^{11d}$ are each independently selected from hydrogen, optionally substituted $C_{1-6}$ alkyl, and optionally substituted aryl which may be substituted by 0-5 moieties;

$R^{12a}$, $R^{12b}$, $R^{12c}$, and $R^{12d}$ are each independently selected from hydrogen, halogen, optionally substituted $C_{1-6}$ alkyl, optionally substituted branched $C_{1-6}$ alkyl, and optionally substituted $C_{1-6}$ alkoxy;

$R^{13}$ is independently selected at each occurrence from a group consisting of optionally substituted $C_{1-10}$ alkyl, optionally substituted branched $C_{1-10}$ alkyl, optionally substituted $C_{3-8}$ cycloalkyl, and optionally substituted aryl which may be substituted by 0-5 moieties;

$R^{14}$ is selected from a group consisting of optionally substituted $C_{1-10}$ alkyl, optionally substituted branched $C_{1-10}$ alkyl, optionally substituted $C_{3-14}$ cycloalkyl, optionally substituted aryl which may be substituted by 0-5 moieties, optionally substituted benzyl which may be substituted by 0-5 moieties, —$CH_2OR^{16}$, $CH(CH_3)OR^{16}$, $CH_2SR^{16}$, $CH_2CH_2SCH_3$, $CH_2CH_2CH_2CH_2NR^{17a}R^{17b}$, $CH_2COR^{18}$, $CH_2CH_2COR^{18}$,

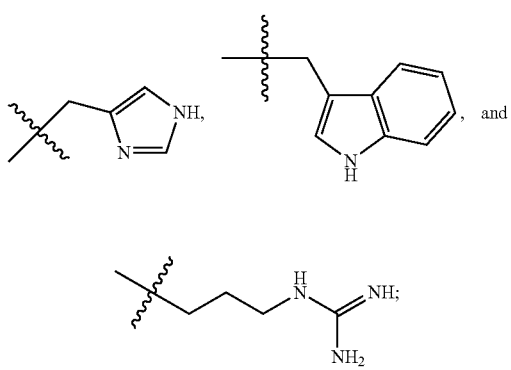

$R^{15}$ is selected from a group consisting of $COR^6$, $CO_2R^7$, $SO_2R^8$, $CONHR^9$, and $P(O)(OR^{10})_2$;

$R^{16}$ is selected from the group consisting of hydrogen, optionally substituted $C_{1-10}$ alkyl, and optionally substituted branched $C_{1-10}$ alkyl;

$R^{17a}$ is selected from the group consisting of hydrogen, optionally substituted $C_{1-10}$ alkyl, and optionally substituted branched $C_{1-10}$ alkyl;

$R^{17b}$ is selected from the group consisting of hydrogen, optionally substituted $C_{1-10}$ alkyl, and optionally substituted branched $C_{1-10}$ alkyl; and $R^{17b}$ is selected from the group consisting of OH, $NH_2$, and $C_{1-6}$ alkoxy; and a hydrate, a solvate, a pharmaceutically acceptable salt, or a complex thereof.

In some embodiments, $R^1$ and $R^2$ are $COR^5$. In other embodiments, $R^5$ is selected from: $OR^{13}$;

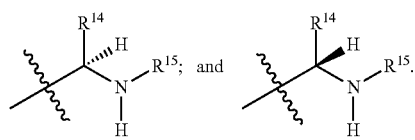

Yet other embodiments provide compounds wherein $R^5$ is $OR^{13}$.

In some embodiments, $R^{13}$ is selected from: optionally substituted $C_{1-10}$ alkyl, optionally substituted branched $C_{1-10}$ alkyl, optionally substituted $C_{3-8}$ cycloalkyl, and optionally substituted aryl which may be substituted by 0-5 moieties.

In some embodiments, $R^3$ is selected from: optionally substituted $C_{1-6}$ alkyl, optionally substituted $C_{3-14}$ cycloalkyl, $COR^6$, $CO_2R^7$, and $CONHR^9$. In other embodiments, $R^3$ is selected from: optionally substituted $C_{1-6}$ alkyl, optionally substituted $C_{3-8}$ cycloalkyl, and $CONHR^9$. In some embodiments, $R^3$ is $CONHR^9$.

In some embodiments, $R^4$ is selected from: optionally substituted $C_{1-6}$ alkyl, optionally substituted $C_{3-14}$ cycloalkyl, and optionally substituted aryl which may be substituted by 0-5 moieties. In some embodiments, $R^4$ is optionally substituted $C_{3-6}$ cycloalkyl.

Further embodiments provide compounds wherein $R^9$ is selected from: hydrogen, optionally substituted $C_{1-10}$ alkyl, optionally substituted branched $C_{1-10}$ alkyl, and optionally substituted $C_{3-14}$ cycloalkyl. In other embodiments, $R^9$ is optionally substituted branched C3-6 alkyl.

Further embodiments provide a compound of formula XXVII(a):

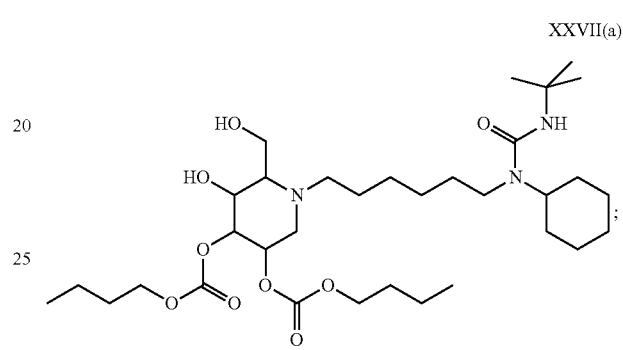

or a pharmaceutically acceptable salt thereof.

Other embodiments provide a compound of formula XXVIII(a):

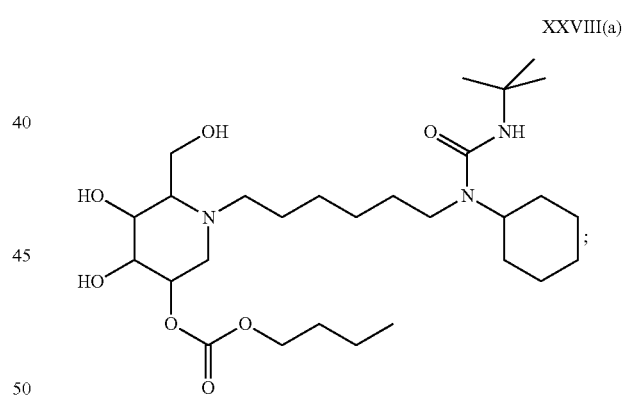

or a pharmaceutically acceptable salt thereof.

Still further embodiments provide a method for treating or preventing a disease or condition associated with a virus selected from an arenavirus, a filovirus, a bunyavirus, and a flavivirus, wherein the disease or condition is selected from: Bovine viral diarrhea virus (BVDV); Dengue virus (DENV); Yellow fever virus (YFV); Ebola virus (EBoV); Marburg virus (MARV); Lassa fever virus (LFV); Tacaribe virus (TARV); and Rift Valley fever virus (RVFV), said method comprising administering to a subject in need thereof, an effective amount of any one of the compounds described herein.

In some embodiments, the present invention provides a compound having the formula XXVIII(b):

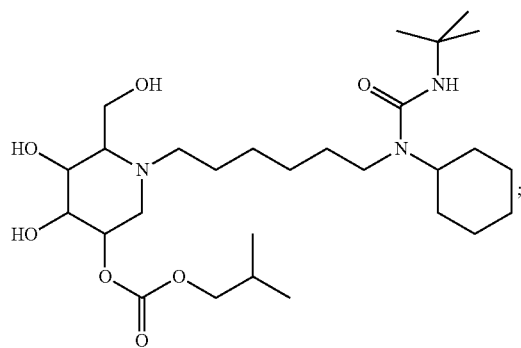

XXVIII(b)

or a pharmaceutically acceptable salt thereof.

Still further embodiments provide a compound having the formula XXX(a):

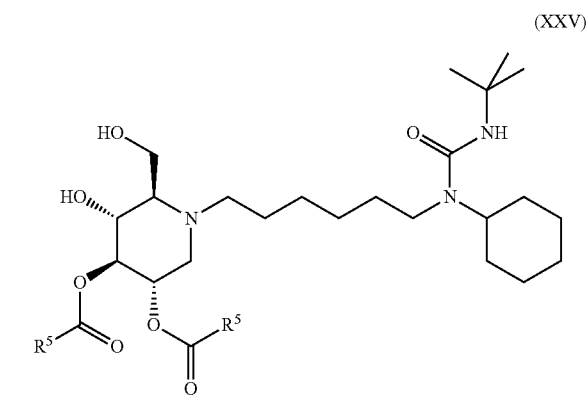

XXX(a)

or a pharmaceutically acceptable salt thereof.

Exemplary embodiments include compounds having the formula (XXV) or a pharmaceutically acceptable salt form thereof:

(XXV)

wherein non-limiting examples of $R^5$ defined herein below in Table 1.

TABLE 1

| Entry | $R^5$ |
|---|---|
| 1 | (phenyl) |
| 2 | (4-fluorophenyl) |
| 3 | $CH_2(CH_2)_5CH_3$ |
| 4 | $CH_2(CH_2)_3CH(CH_3)_2$ |

Exemplary embodiments include compounds having the formula (XXVI) or a pharmaceutically acceptable salt form thereof:

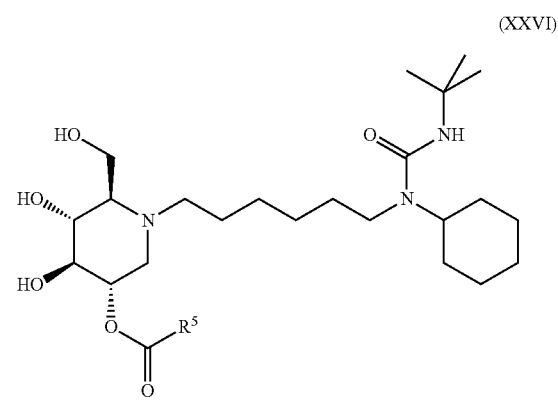

(XXVI)

wherein non-limiting examples of $R^5$ are defined herein below in Table 2.

TABLE 2

| Entry | $R^5$ |
|---|---|
| 1 | (phenyl) |
| 2 | (4-fluorophenyl) |
| 3 | $CH_2(CH_2)_5CH_3$ |
| 4 | $CH_2(CH_2)_3CH(CH_3)_2$ |

Exemplary embodiments include compounds having the formula (XXVII) or a pharmaceutically acceptable salt form thereof:

(XXVII)

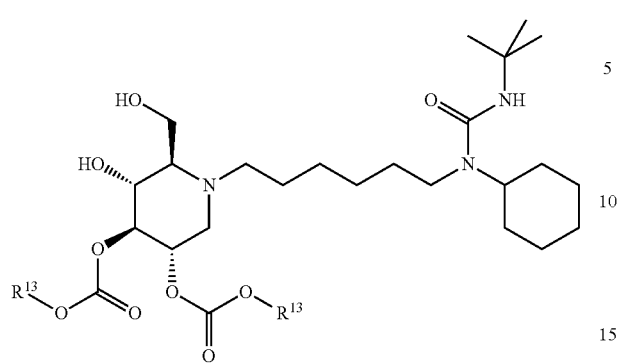

wherein non-limiting examples of R" are defined herein below in Table 3.

TABLE 3

| Entry | $R^{13}$ |
|---|---|
| 1 | (phenyl-CH<) |
| 2 | $CH_2(CH_2)_2CH_3$ |
| 3 | $CH_2CH(CH_3)_2$ |

Exemplary embodiments include compounds having the formula (XXVIII) or a pharmaceutically acceptable salt form thereof:

(XXVIII)

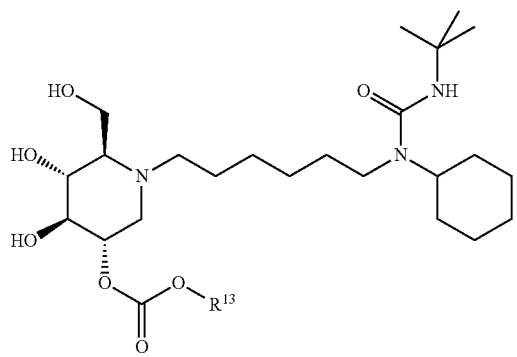

wherein non-limiting examples of $R^{13}$ are defined herein below in Table 4.

TABLE 4

| Compound | $R^{13}$ |
|---|---|
| 12 | (phenyl-CH<) |
| 13 | $CH_2(CH_2)_2CH_3$ |
| 14 | $CH_2CH(CH_3)_2$ |

Exemplary embodiments include compounds having the formula (XXIX) or a pharmaceutically acceptable salt form thereof:

(XXIX)

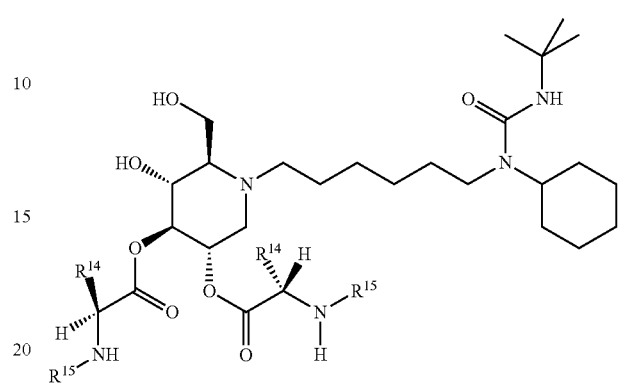

wherein non-limiting examples of $R^{14}$ and $R^{15}$ are defined herein below in Table 5.

TABLE 5

| Entry | $R^{14}$ | $R^{15}$ |
|---|---|---|
| 1 | (benzyl) | $CO_2C(CH_3)_3$ |
| 2 | Me | $CO_2C(CH_3)_3$ |
| 3 | $CH(CH_3)_2$ | $CO_2C(CH_3)_3$ |
| 4 | $CH(CH_3)CH_2CH_3$ | $CO_2C(CH_3)_3$ |
| 5 | $CH_2CH(CH_3)_2$ | $CO_2C(CH_3)_3$ |
| 6 | H | $CO_2C(CH_3)_3$ |

Exemplary embodiments include compounds having the formula (XXX) or a pharmaceutically acceptable salt form thereof:

(XXX)

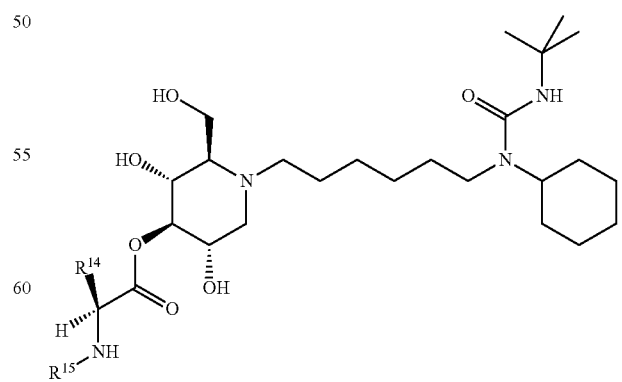

wherein non-limiting examples of $R^{14}$ and $R^{15}$ are defined herein below in Table 6.

TABLE 6

| Entry | $R^{14}$ | $R^{15}$ |
|---|---|---|
| 1 | benzyl (CH$_2$Ph with branch) | $CO_2C(CH_3)_3$ |
| 2 | Me | $CO_2C(CH_3)_3$ |
| 3 | $CH(CH_3)_2$ | $CO_2C(CH_3)_3$ |
| 4 | $CH(CH_3)CH_2CH_3$ | $CO_2C(CH_3)_3$ |
| 5 | $CH_2CH(CH_3)_2$ | $CO_2C(CH_3)_3$ |
| 6 | H | $CO_2C(CH_3)_3$ |

For the purposes of demonstrating the manner in which the compounds of the present invention are named and referred to herein, the compound having the formula:

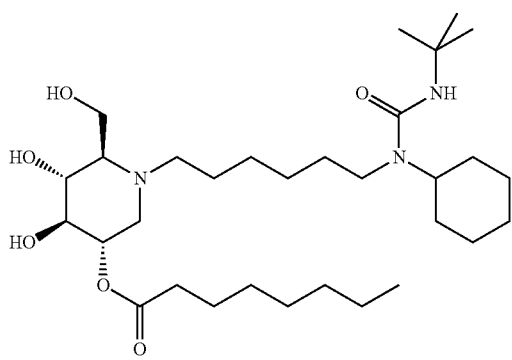 [SMILES: CCCCCCCC(=O)O[C@H]1CN(CCCCCCN(C(=O)NC(C)(C)C)C2CCCCC2)[C@H](CO)[C@@H](O)[C@@H]1O]

has the chemical name (3 S,4S,5R,6R)-1-(6-(3-(tert-butyl)-1-cyclohexylureido)hexyl)-4,5-dihydroxy-6-(hydroxymethyl)piperidin-3-yl octanoate.

For the purposes of demonstrating the manner in which the compounds of the present invention are named and referred to herein, the compound having the formula:

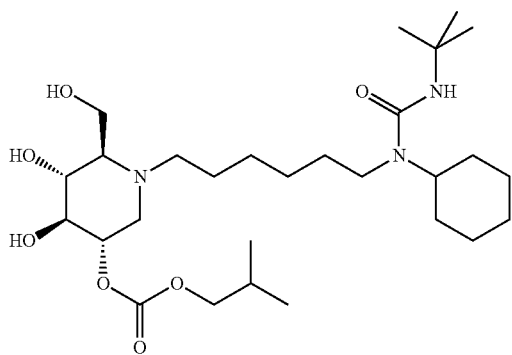 [SMILES: CC(C)COC(=O)O[C@H]1CN(CCCCCCN(C(=O)NC(C)(C)C)C2CCCCC2)[C@H](CO)[C@@H](O)[C@@H]1O]

has the chemical name (3S,4S,5R,6R)-1-(6-(3 -(tert-butyl)-1-cyclohexylureido)hexyl)-4,5-dihydroxy-6-(hydroxymethyl)piperidin-3-yl i sobutyl carbonate.

For the purposes of demonstrating the manner in which the compounds of the present invention are named and referred to herein, the compound having the formula:

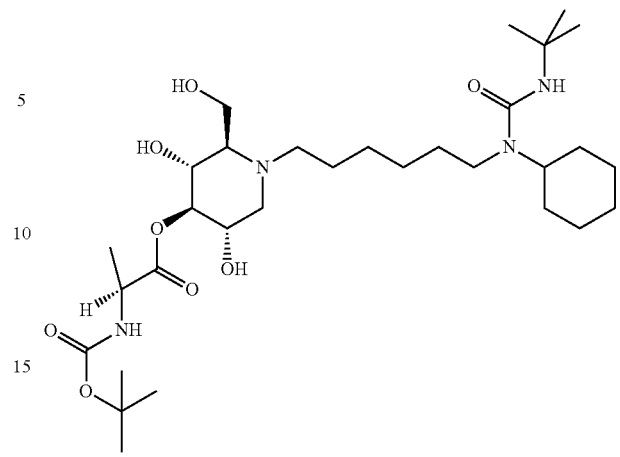

has the chemical name(S)-(2R,3R,4R,5S)-1-(6-(3-(tert-butyl)-1-cyclohexylureido) hexyl)-3,5-dihydroxy-2-(hydroxymethyl)piperidin-4-yl 2-((tert-butoxycarbonyl)amino) propanoate.

For the purposes of the present invention, a compound depicted by the diastereomeric formula, for example:

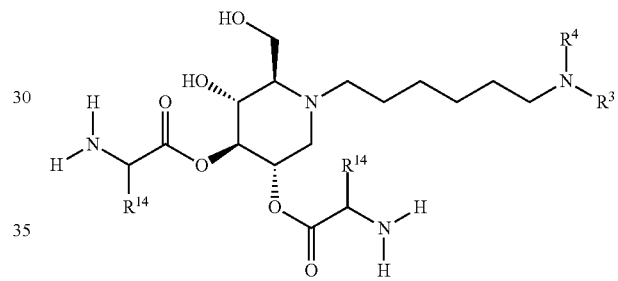

will stand equally well for either of the four diasteromers having the formula:

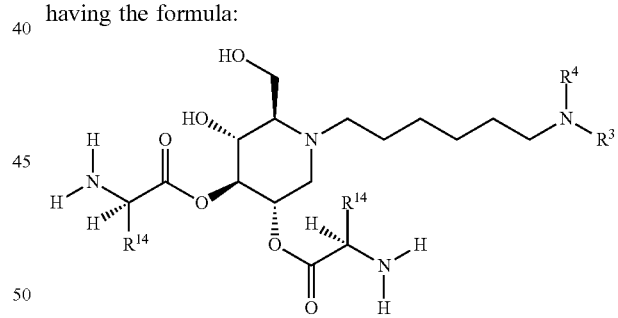

or the formula:

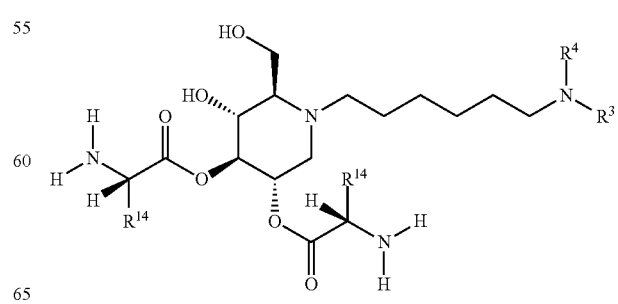

or the formula:

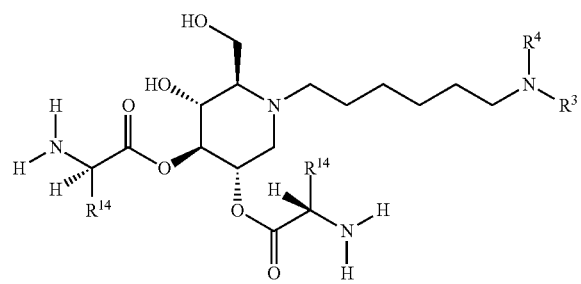

or the formula:

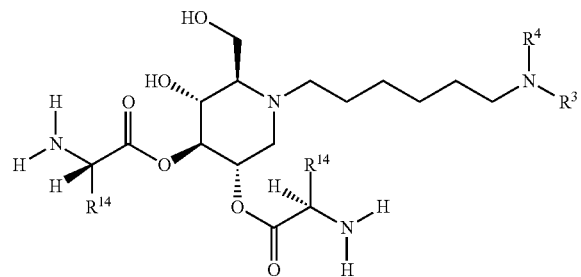

or mixtures thereof.

In all of the embodiments provided herein, examples of suitable optional substituents are not intended to limit the scope of the claimed invention. The compounds of the invention may contain any of the sub stituents, or combinations of substituents, provided herein.

The present invention further relates to a process for preparing the novel alkylated imino sugars of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The reagents used in the preparation of the compounds of this invention can be either commercially obtained or can be prepared by standard procedures described in the literature. In accordance with this invention, compounds in the genus may be produced by one of the following reaction schemes.

The first aspect of the process of the present invention relates to a process for preparing novel alkylated imino sugars having the formula (I). Compounds of formula (I) may be prepared according to the process outlined in Scheme 1.

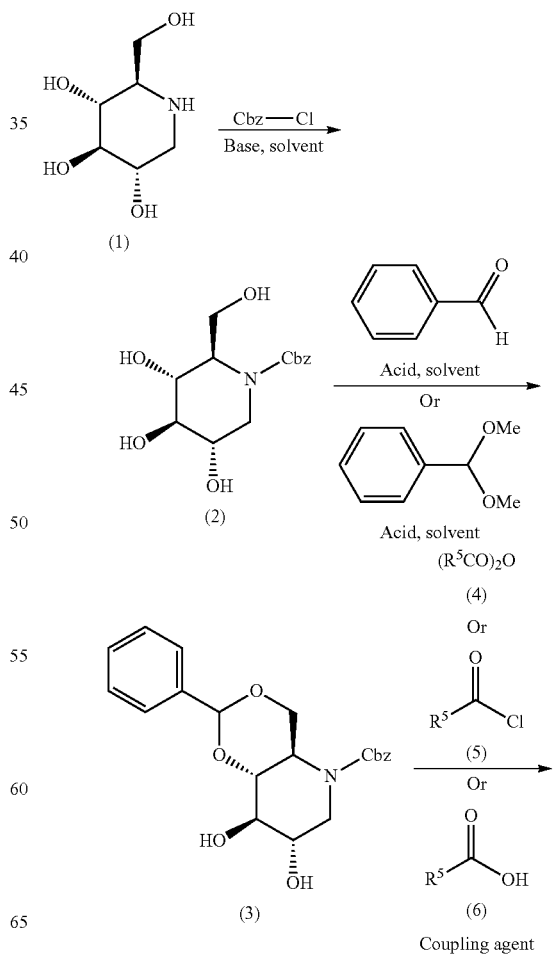

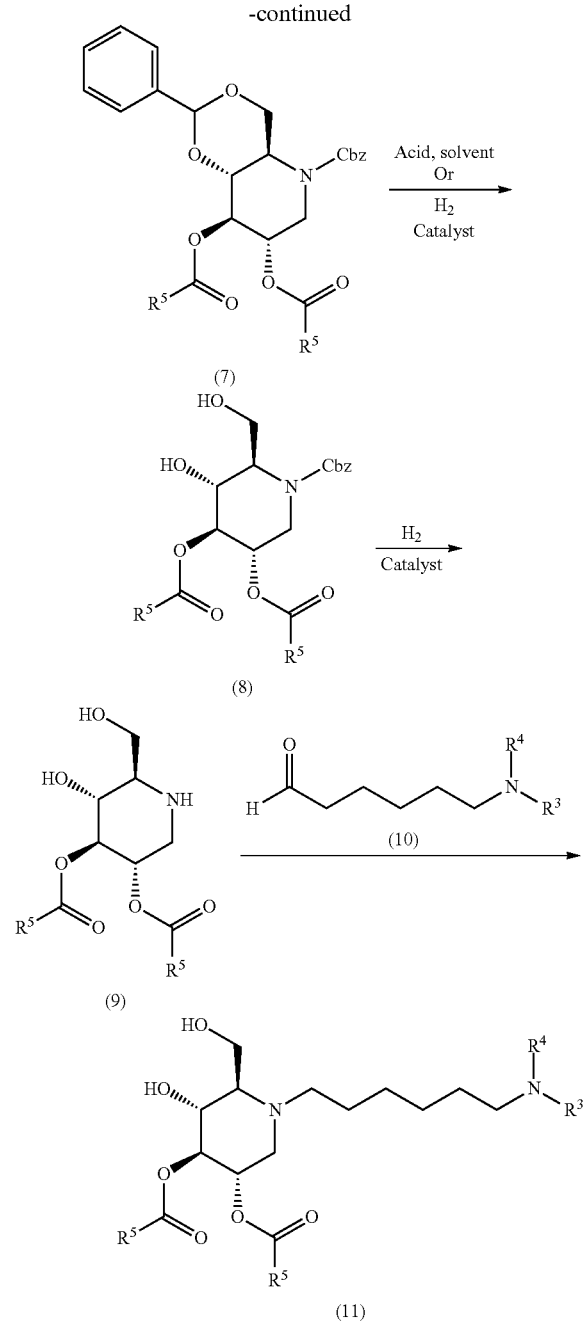

pound of the formula (3). Alternatively, a compound of the formula (2) is then reacted with (dimethoxymethyl)benzene in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (3). A compound of the formula (3) is then reacted with a compound of the formula (4), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (7). Alternatively, a compound of the formula (3) is then reacted with a compound of the formula (5), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (7). Alternatively, a compound of the formula (3) is then reacted with a compound of the formula (6), a known compound or a compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (7). A compound of the formula (7) is then reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (8). Alternatively, a compound of the formula (7) is then reacted with hydrogen in the presence of a catalyst such as as palladium (II) acetate, tetraki s(triphenylphosphine)palladium(0), dichlorobis (triphenylphosphine) palladium(II), palladium on carbon, bis (acetonitrile)dichloropalladium(II), and the like, in the presence of a solvent such as methanol, ethanol, tetrahydrofuran, 1,4-dioxane, and the like, optionally with heating, optionally with microwave irradiation to give a compound of the formula (8). A compound of the formula (8) is then reacted with hydrogen in the presence of a catalyst such as as palladium (II) acetate, tetrakis(triphenylphosphine)palladium(0), dichlorobis (triphenylphosphine)palladium(II), palladium on carbon, bis(acetonitrile)dichloropalladium(II), and the like, in the presence of a solvent such as methanol, ethanol, tetrahydrofuran, 1,4-dioxane, and the like, optionally with heating, optionally with microwave irradiation to give a compound of the formula (9). A compound of the formula (9) is then reacted with a compound of the formula (10), a known compound or a compound prepared by known methods, in the presence of a reducing agent such as sodium borohydride, sodium cyanoborohydride, sodium triacetoxy- Accordingly, a suitably substituted compound of the formula (1), a known compound or compound prepared by known methods, is reacted with benzyl chloroformate in the presence of a base such as potassium carbonate, sodium carbonate, cesium carbonate, triethyl amine, pyridine, sodium hydride, and the like, in an organic solvent such as ethyl acetate, acetonitrile, tetrahydronfuran, 1,4-dioxane, dimethylformamide, methylene chloride, dichloroethane, and the like, optionally in the presence of water, optionally with heating, optionally with microwave irradiation to give a compound of the formula (2). A compound of the formula (2) is then reacted with benzaldehyde in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a comborohydride, lithium borohydride, and the like, optionally in the presence of an acid such as acetic acid, trifluoroaceatic acid, hydrochloric acid, and the like, in the presence of a solvent such as methanol, ethanol, tetrahydrofuran, 1,4-dioxane, and the like, optionally with heating, optionally with microwave irradiation to give a compound of the formula (11).

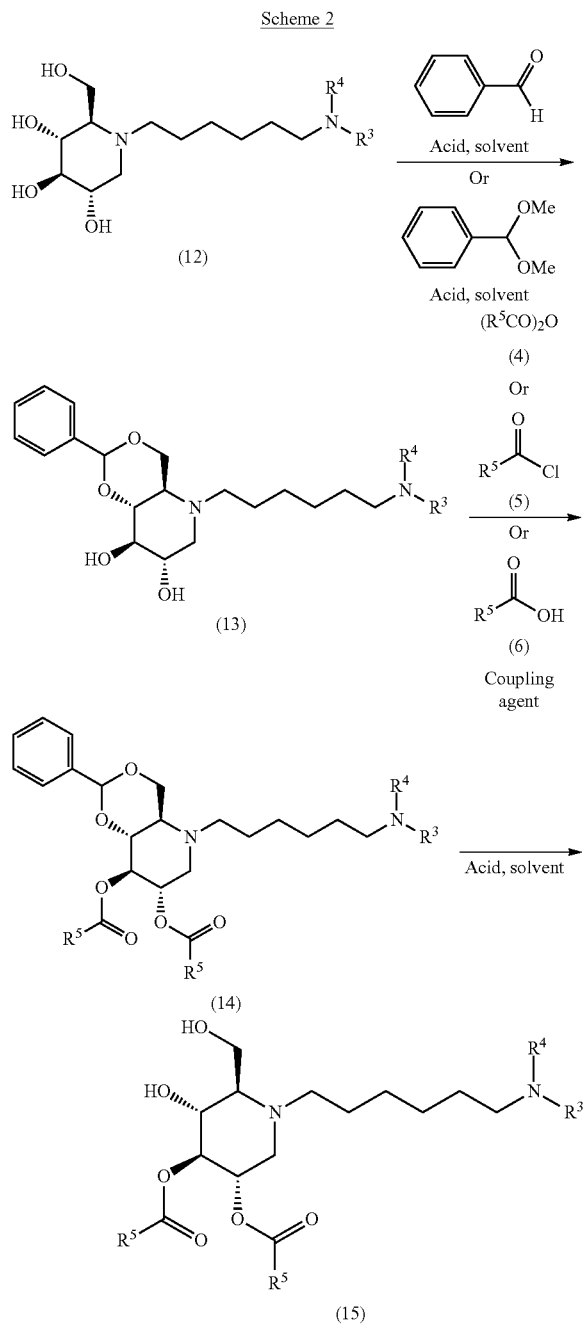

Alternatively, a compound of the formula (12), a known compound or a compound prepared by known methods, is reacted with benzaldehyde in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, option-ally with microwave irradiation to give a compound of the formula (13). Alternatively, a compound of the formula (2) is then reacted with (dimethoxymethyl)benzene in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (13). A compound of the formula (13) is then reacted with a compound of the formula (4), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (14). Alternatively, a compound of the formula (13) is then reacted with a compound of the formula (5), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (14). Alternatively, a compound of the formula (13) is then reacted with a compound of the formula (6), a known compound or a compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N', N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (14). A compound of the formula (14) is then reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (15).

Scheme 3

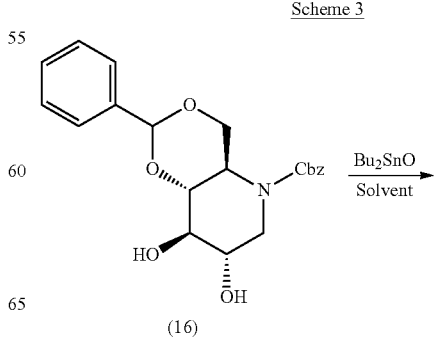

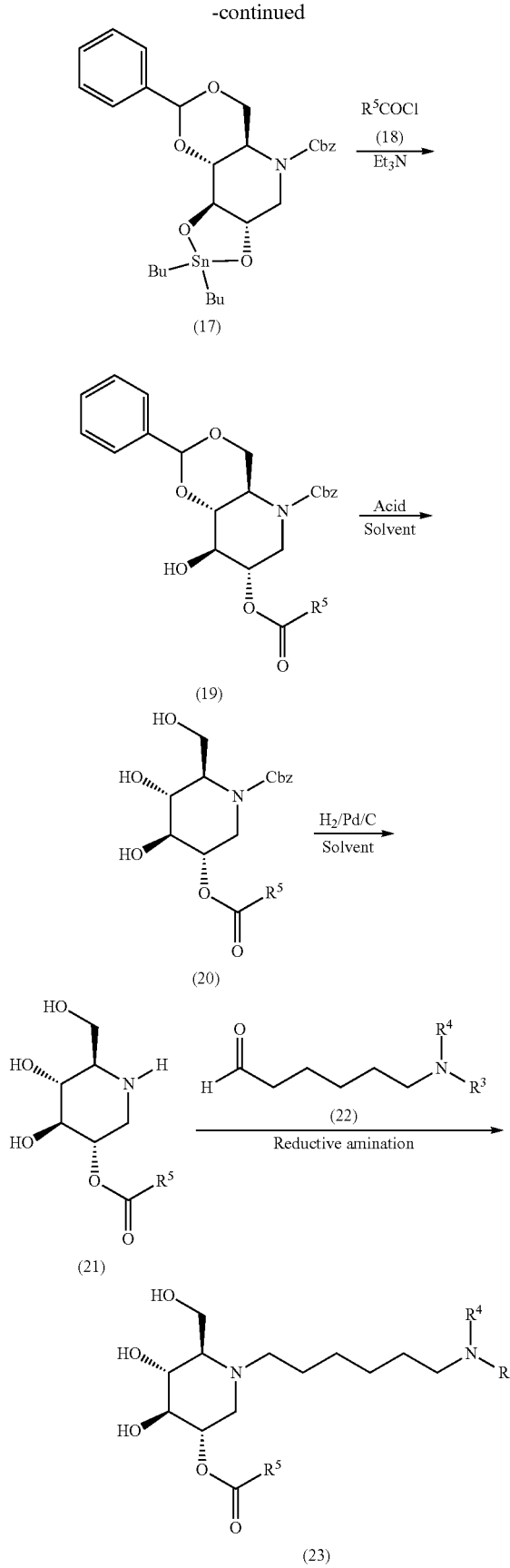

A compound of the formula (16) is reacted with a dialkyl tin oxide such as dibutyl tin oxide or a dialkyl tin dichloride such as dibutyl tin dichloride, in an organic solvent such as toluene, xylene, methanol, 1,4-dioxane, dimethylformamide and the like, optionally with heating, optionally with microwave irradiation to give a compound of the formula (17). A compound of the formula (17) is is then reacted with a compound of the formula (18), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (19). A compound of the formula (19) is reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (20). A compound of the formula (20) is then reacted with hydrogen in the presence of a catalyst such as as palladium (II) acetate, tetrakis(triphenylphosphine)palladium(0), dichlorobis (triphenylphosphine) palladium(II), palladium on carbon, bis (acetonitrile)dichloropalladium(II), and the like, in the presence of a solvent such as methanol, ethanol, tetrahydrofuran, 1,4-dioxane, and the like, optionally with heating, optionally with microwave irradiation to give a compound of the formula (21). A compound of the formula (21) is then reacted with a compound of the formula (22), a known compound or a compound prepared by known methods, in the presence of a reducing agent such as sodium borohydride, sodium cyanoborohydride, sodium triacetoxyborohydride, lithium borohydride, and the like, optionally in the presence of an acid such as acetic acid, trifluoroaceatic acid, hydrochloric acid, and the like, in the presence of a solvent such as methanol, ethanol, tetrahydrofuran, 1,4-dioxane, and the like, optionally with heating, optionally with microwave irradiation to give a compound of the formula (23).

Scheme 4

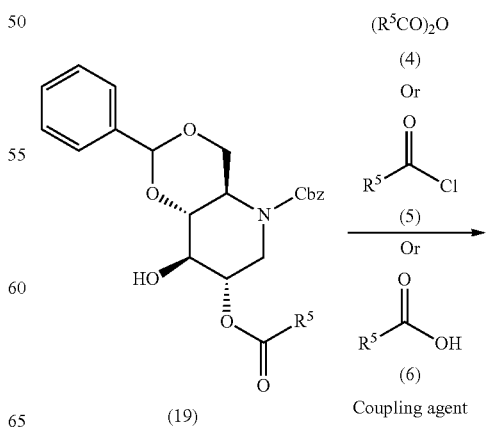

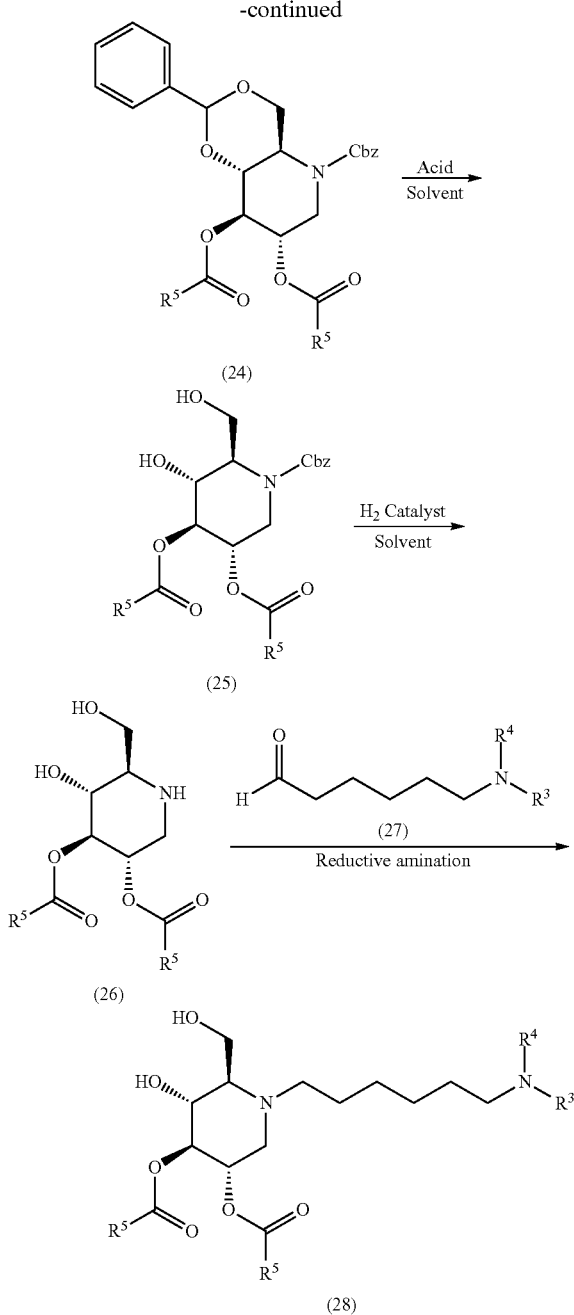

N,N-dimethylformamide, and the like, optionally with heating optionally with microwave irradiation to give a compound of the formula (24). Alternatively, a compound of the formula (19) is then reacted with a compound of the formula (6), a known compound or a compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (24). A compound of the formula (24) is reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (25). A compound of the formula (25) is then reacted with hydrogen in the presence of a catalyst such as as palladium (II) acetate, tetrakis(triphenylphosphine)palladium(0), dichlorobis (triphenylphosphine) palladium(II), palladium on carbon, bis(acetonitrile)dichloropalladium(II), and the like, in the presence of a solvent such as methanol, ethanol, tetrahydrofuran, 1,4-dioxane, and the like, optionally with heating, optionally with microwave irradiation to give a compound of the formula (26). A compound of the formula (26) is then reacted with a compound of the formula (27), a known compound or a compound prepared by known methods, in the presence of a reducing agent such as sodium borohydride, sodium cyanoborohydride, sodium triacetoxyborohydride, lithium borohydride, and the like, optionally in the presence of an acid such as acetic acid, trifluoroaceatic acid, hydrochloric acid, and the like, in the presence of a solvent such as methanol, ethanol, tetrahydrofuran, 1,4-dioxane, and the like, optionally with heating, optionally with microwave irradiation to give a compound of the formula (28).

Alternatively, a compound of the formula (19) is then reacted with a compound of the formula (4), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (24). Alternatively, a compound of the formula (19) is then reacted with a compound of the formula (5), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, Scheme 5

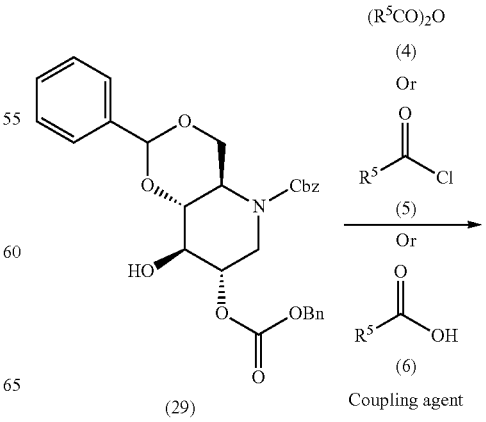

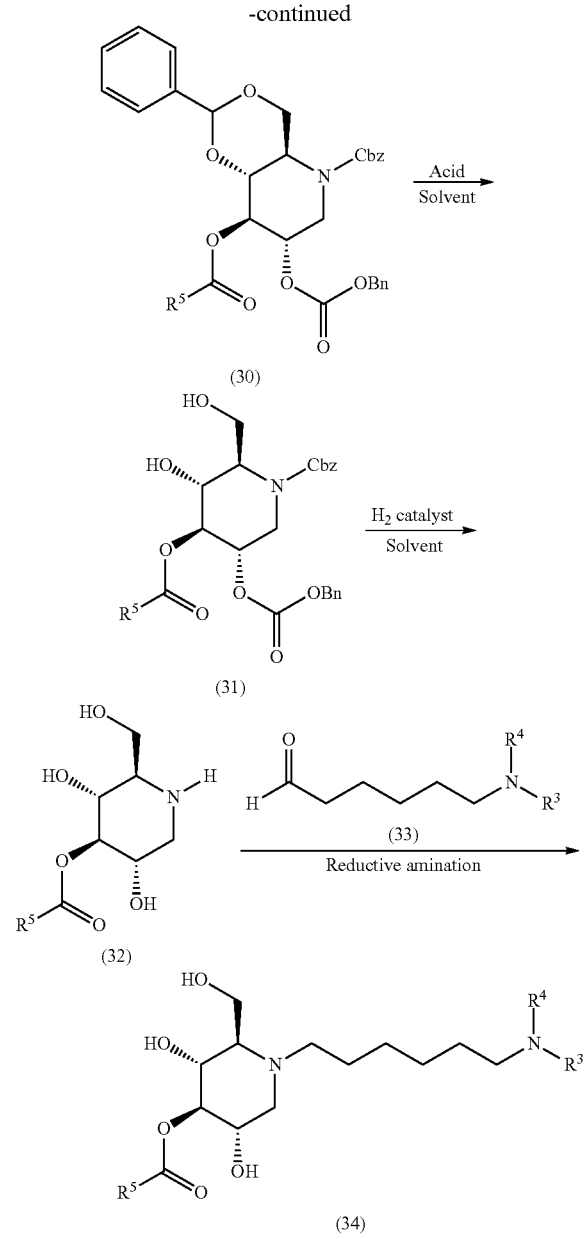

(30)

(31)

(32)

(34)

A compound of the formula (29) is reacted with a compound of the formula (4), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (30). Alternatively, a compound of the formula (29) is then reacted with a compound of the formula (5), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (30). Alternatively, a compound of the formula (29) is then reacted with a compound of the formula (6), a known compound or a compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (30). A compound of the formula (30) is reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (31). A compound of the formula (31) is then reacted with hydrogen in the presence of a catalyst such as as palladium (II) acetate, tetrakis(triphenylphosphine)palladium(0), dichlorobis (triphenylphosphine)palladium(II), palladium on carbon, bis(acetonitrile)dichloropalladium(II), and the like, in the presence of a solvent such as methanol, ethanol, tetrahydrofuran, 1,4-dioxane, and the like, optionally with heating, optionally with microwave irradiation to give a compound of the formula (32). A compound of the formula (32) is then reacted with a compound of the formula (33), a known compound or a compound prepared by known methods, in the presence of a reducing agent such as sodium borohydride, sodium cyanoborohydride, sodium triacetoxyborohydride, lithium borohydride, and the like, optionally in the presence of an acid such as acetic acid, trifluoroaceatic acid, hydrochloric acid, and the like, in the presence of a solvent such as methanol, ethanol, tetrahydrofuran, 1,4-dioxane, and the like, optionally with heating, optionally with microwave irradiation to give a compound of the formula (34).

Scheme 6

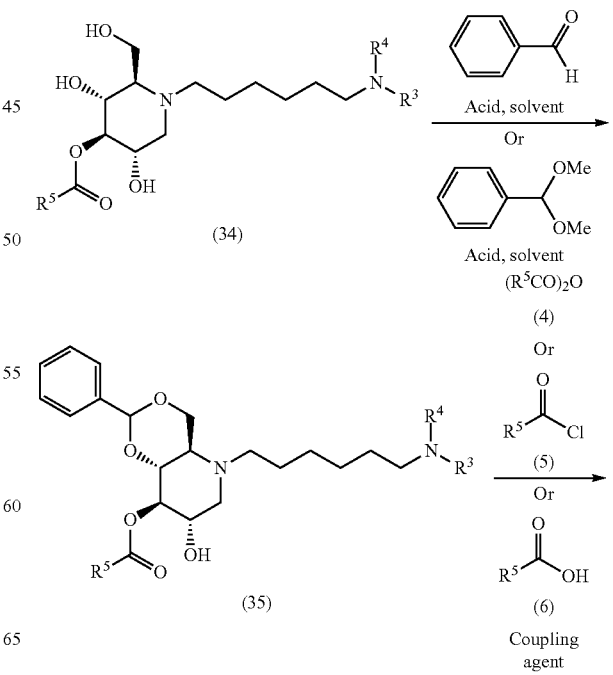

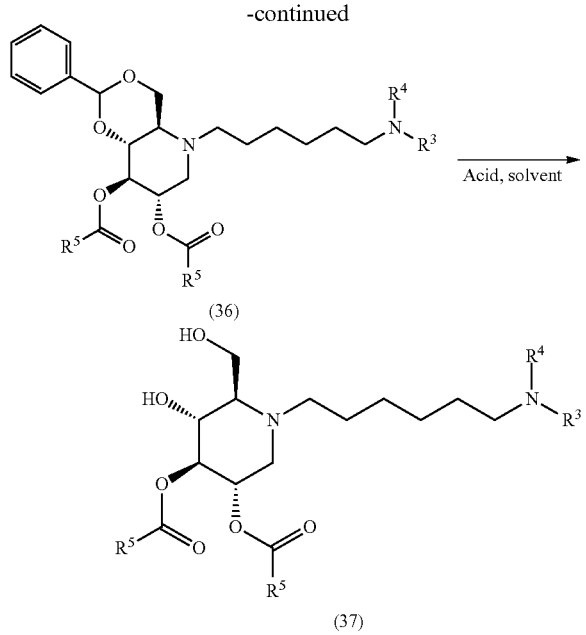

(36)

(37)

A compound of the formula (34), a known compound or a compound prepared by known methods, is reacted with benzaldehyde in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (35). Alternatively, a compound of the formula (34) is then reacted with (dimethoxymethyl)benzene in the presence of an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (35). A compound of the formula (35) is reacted with a compound of the formula (4), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (36). Alternatively, a compound of the formula (35) is then reacted with a compound of the formula (5), a known compound or a compound prepared by known methods, in the presence of a base such as triethylamine, diisopropylethylamine, pyridine, 2,6-lutidine and the like, in a solvent such as methylene chloride, 1,2-dichloroethane, tetrahydrofuran, 1,6-dioxane, N,N-dimethylformamide, and the like, optionally with heating optionally with microwave irradiation to give a compound of the formula (36). Alternatively, a compound of the formula (35) is then reacted with a compound of the formula (6), a known compound or a compound prepared by known methods, in the presence of coupling agent such as such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide a compound of the formula (36). A compound of the formula (36) is reacted with an acid such as hydrochloric acid, sulfuric acid, trifluoroacetic acid, acetic acid, and the like, in a solvent such as methanol, ethanol, tetrahydrofuran, 1,4-dioxane, toluene, methylene chloride, dichloroethane, and the like, optionally with heating, optionally with microwave irradiation to give a compound of the formula (37).

Scheme 7

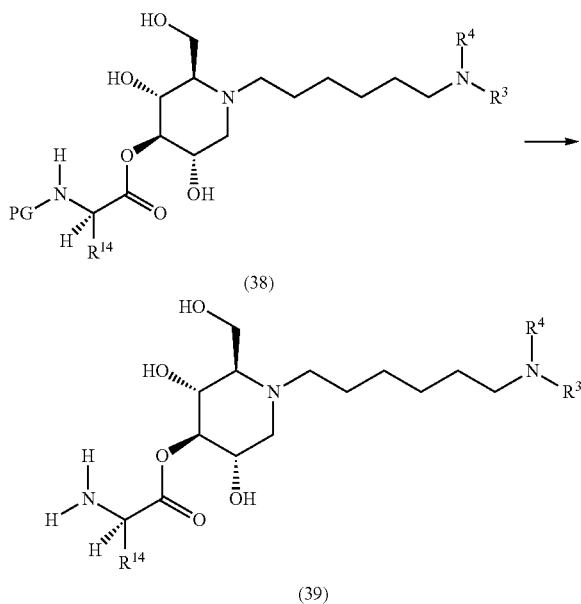

(38)

(39)

A compound of the formula (38) wherein PG is a protecting group such as tert-butyloxycarbonyl (BOC), Carbobenzyloxy (Cbz), 9-Fluorenylmethyloxycarbonyl (FMOC), p-Methoxybenzyl carbonyl (Moz or MeOZ), and the like, is deprotected using one of the following means. A compound of the formula (38) is reacted with an acid such as trifluoroacetic acid, acetic acid, hydrochloric acid, and the like in the presence of a solvent such as methylene chloride, tetrahydrofuran, 1,4-dioxane, methanol, ethanol, N,N-dimethylformamide, and the like, optionally with heating, optionally with microwave irradiation and the like to provide a compound of the formula (39). Alternatively, a compound of the formula (38) is reacted with hydrogen in the presence of a catalyst such as as palladium (II) acetate, tetraki s(triphenylphosphine)palladium(0), dichlorobis (triphenylphosphine)palladium(II), palladium on carbon, bis (acetonitrile)dichloro palladium(II), and the like, in the presence of a solvent such as methanol, ethanol, tetrahydrofuran, 1,4-dioxane, and the like, optionally with heating, optionally with microwave irradiation to give a compound of the formula (39). Alternatively, a compound of the formula (38) is reacted with a base such as piperidine, diisopropylethylamine, triethylamine, pyridine, and the like in the presence of a solvent such as methylene chloride, tetrahydrofuran, 1,4-dioxane, ethanol, methanol, and the like optionally with heating, optionally with microwave irradiation to provide a compound of the formula (39). In the event that one or more of the chiral centers shown in a compound of the formula (38) are inverted, one skilled in the art would recognize that the conditions described herein could be used to remove said protecting groups.

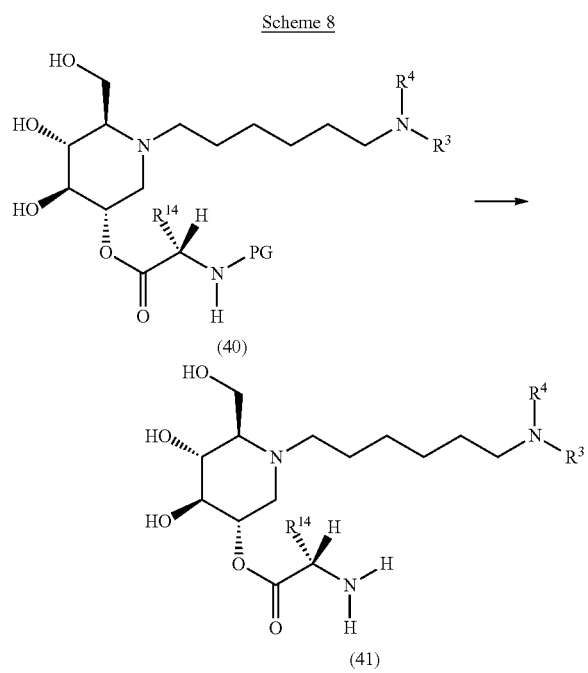

A compound of the formula (40) wherein PG is a protecting group such as tert-butyloxycarbonyl (BOC), Carbobenzyloxy (Cbz), 9-Fluorenylmethyloxycarbonyl (FMOC), p-Methoxybenzyl carbonyl (Moz or MeOZ), and the like, is deprotected using one of the following means. A compound of the formula (40) is reacted with an acid such as trifluoroacetic acid, acetic acid, hydrochloric acid, and the like in the presence of a solvent such as methylene chloride, tetrahydrofuran, 1,4-dioxane, methanol, ethanol, N,N-dimethylformamide, and the like, optionally with heating, optionally with microwave irradiation and the like to provide a compound of the formula (41). Alternatively, a compound of the formula (40) is reacted with hydrogen in the presence of a catalyst such as as palladium (II) acetate, tetraki s(triphenylphosphine)palladium(0), dichlorobis (triphenylphosphine)palladium(II), palladium on carbon, bis (acetonitrile)dichloro palladium(II), and the like, in the presence of a solvent such as methanol, ethanol, tetrahydrofuran, 1,4-dioxane, and the like, optionally with heating, optionally with microwave irradiation to give a compound of the formula (41). Alternatively, a compound of the formula (40) is reacted with a base such as piperidine, diisopropylethylamine, triethylamine, pyridine, and the like in the presence of a solvent such as methylene chloride, tetrahydrofuran, 1,4-dioxane, ethanol, methanol, and the like optionally with heating, optionally with microwave irradiation to provide a compound of the formula (41). In the event that one or more of the chiral centers shown in a compound of the formula (40) are inverted, one skilled in the art would recognize that the conditions described herein could be used to remove said protecting groups.

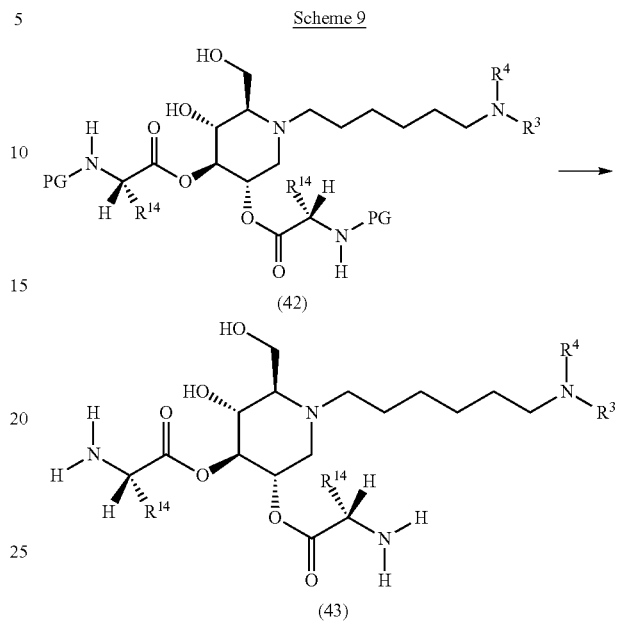

A compound of the formula (42) wherein PG is a protecting group such as tert-butyloxycarbonyl (BOC), Carbobenzyloxy (Cbz), 9-Fluorenylmethyloxycarbonyl (FMOC), p-Methoxybenzyl carbonyl (Moz or MeOZ), and the like, is deprotected using one of the following means. A compound of the formula (42) is reacted with an acid such as trifluoroacetic acid, acetic acid, hydrochloric acid, and the like in the presence of a solvent such as methylene chloride, tetrahydrofuran, 1,4-dioxane, methanol, ethanol, N,N-dimethylformamide, and the like, optionally with heating, optionally with microwave irradiation and the like to provide a compound of the formula (43). Alternatively, a compound of the formula (42) is reacted with hydrogen in the presence of a catalyst such as as palladium (II) acetate, tetraki s(triphenylphosphine)palladium(0), dichlorobis (triphenylphosphine)palladium(II), palladium on carbon, bis (acetonitrile)dichloro palladium(II), and the like, in the presence of a solvent such as methanol, ethanol, tetrahydrofuran, 1,4-dioxane, and the like, optionally with heating, optionally with microwave irradiation to give a compound of the formula (43). Alternatively, a compound of the formula (42) is reacted with a base such as piperidine, diisopropylethylamine, triethylamine, pyridine, and the like in the presence of a solvent such as methylene chloride, tetrahydrofuran, 1,4-dioxane, ethanol, methanol, and the like optionally with heating, optionally with microwave irradiation to provide a compound of the formula (43). If a compound of the formula (42) contains two protecting groups (PG) that may be removed under different conditions, one skilled in the art would know how to selectively removes each protecting group sequentially using the conditions described herein. In the event that one or more of the chiral centers shown in a compound of the formula (42) are inverted, one skilled in the art would recognize that the conditions described herein could be used to remove said protecting groups.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

The present invention also relates to compositions or formulations which comprise the glucosidase inhibitors according to the present invention. In general, the compositions of the present invention comprise an effective amount of one or more alkylated imino sugars and salts thereof according to the present invention which are effective for providing glucosidase inhibition; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known anti-viral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more alkylated imino sugars according to the present invention and one or more excipients; from about 0.01 mg to about 100 mg of one or more alkylated imino sugars according to the present invention and one or more excipients; and from about 0.1 mg to about 10 mg of one or more alkylated imino sugars according to the present invention; and one or more excipients.

Embodiments of the present invention will now be described in conjunction with the following, non-limiting examples.

EXAMPLES

Example 1

The stability of exemplary compounds of the present invention and their conversion to their active derivatives in simulated gastric fluid is evaluated. The working solutions of test compounds and control compound erythromycin were prepared in DMSO at the concentration of 500 µM. 2 µL of the working solution and 198 µL of simulated gastric fluids were added into centrifuge tubes to achieve a final concentration of 5 and incubated at 37° C. water bath with shaking at approximately 60 rpm. One of the centrifuge tubes was taken at designated time points including 0, 30, 60, 90 and 120 minutes. The assay was performed in duplicate. The reaction was stopped by adding 5 volumes of cold quench solution (acetonitrile containing internal standards (IS, 100 nM Alprazolam, 500 nM Labetalol and 2 µM Ketoprofen)) to the spiked simulated gastric fluids samples at the appointed time points. Another time 0 samples of parent compound were also prepared, and they were used to calculate the conversion percentages of prodrugs to parent compound (used as T0-2). Samples were vortexed for 2 minutes and centrifuged at 20,000 g for 15 minutes at 4° C. to precipitate protein. And then 50 µL of the supernatant was transferred to a new 96-well plate with 100 µL quench solution and 100 µL water for LC-MS/MS analysis. The results of these evaluations are described below in Table 7.

TABLE 7

| Compound | Stability in Gastric fluids (4 h, %) | |
|---|---|---|
| | Remaining | Converted |
| XXVII(a) | 93 | 0.01 |
| XXVIII(a) | 98.1 | 0.05 |
| XXVIII(b) | 89.2 | 0.06 |
| XXX(a) | 81.1 | 0.4 |

The data described in Table 7 (above), demonstrates that exemplary compounds of the present invention remain largely intact (>80%) in gastric fluid; and therefore, avoid pre-mature conversion to enzymatic active forms before reaching the desired target site.

Example 2

The stability of exemplary compounds of the present invention and their conversion to active derivatives in simulated intestinal fluids is evaluated. The working solutions of test compounds and control compound chlorambucil were prepared in DMSO at the concentration of 500 µM. 2 µL of the working solution and 198 µL of simulated intestinal fluids were added into centrifuge tubes to achieve a final concentration of 5 µM, and incubated at 37° C. water bath with shaking at approximately 60 rpm. One of the centrifuge tubes was taken at designated time points including 0, 1, 2, 3 and 4 hours. The assay was performed in duplicate. The reaction was stopped by adding 5 volumes of cold quench solution (acetonitrile containing internal standards (IS, 100 nM Alprazolam, 500 nM Labetalol and 2 µM Ketoprofen)) to the spiked simulated intestinal fluids samples at the appointed time points. Another time 0 samples of parent compound were also prepared, and they were used to calculate the conversion percentages of prodrugs to parent compound (used as T0-2). Samples were vortexed for 2 minutes and centrifuged at 20,000 g for 15 minutes at 4° C. to precipitate protein. And then 50 µL of the supernatant was transferred to a new 96-well plate with 100 µL quench solution and 100 µL water for LC-MS/MS analysis. The results of these evaluations are described below in Table 8.

TABLE 8

| Compound | Stability in Intestinal Fluid (4 h, %) | |
|---|---|---|
| | Remaining | Converted |
| XXVII(a) | 65.7 | 3.31 |
| XXVIII(a) | 62.7 | 32.2 |
| XXVIII(b) | 70.9 | 30.2 |
| XXX(a) | 30.7 | 77.9 |

The data described in Table 8 (above) demonstrates the ability of exemplary compounds of the present invention to remain intact in the intestinal fluid. The greater the % remaining, the greater the likelihood that a compound will avoid pre-mature conversion to enzymatic active forms before reaching its desired target site.

Example 3

The metabolic stability of exemplary compounds of the present invention in pooled human and male mouse liver microsomes is evaluated. Two separate experiments were performed as follows. a) With Cofactors (NADPH and UDPGA): 10 µL of 20 mg/mL liver microsomes, 40 µL of 10 mM NADPH and 40 µL of 50 mM UDPGA were added to the incubations. The final concentrations of microsomes, NADPH and UDPGA were 0.5 mg/mL, 1 mM and 5 mM, respectively. b) Without Cofactors (NADPH and UDPGA): 10 µL of 20 mg/mL liver microsomes and 80 µL of ultra-pure $H_2O$ were added to the incubations. The final concentration of microsomes was 0.5 mg/mL. The reaction was started with the addition of 4 µL of 200 µM control compound or test compound solutions. Verapamil was used as positive control in this study. The final concentration of test compound or control compound was 2 µM. Aliquots of 50 µL were taken from the reaction solution at 0, 15, 30, 45 and 60 min. The reaction was stopped by the addition of 4 volumes of cold acetonitrile with IS (100 nM Alprazolam, 200 nM Labetalol and 2 µM Ketoprofen). Samples were centrifuged at 3, 220 g for 40 minutes. Aliquot of 90 µL of the supernatant was mixed with 90 μL of ultra-pure H$_2$O and then used for LC-MS/MS analysis. The results of these evaluations are described below in Table 9.

TABLE 9

| Compound | Conversion in Pooled Liver Microsome (1 h, %) | | | |
| --- | --- | --- | --- | --- |
| | With co-factor | | Without cofactor | |
| | H | M | H | M |
| XXVII(a) | 2.94 | 17.2 | 35.1 | 72.1 |
| XXVIII(a) | 6.62 | 39.6 | 46.6 | 97.6 |
| XXVIII(b) | 5.64 | 28.3 | 41.2 | 89.7 |
| XXX(a) | 25.7 | 30.6 | 75.9 | 81.3 |

The data described in Table 9 (above), demonstrate that exemplary compounds of the present invention can be converted to active derivatives by the liver.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A compound having formula (I):

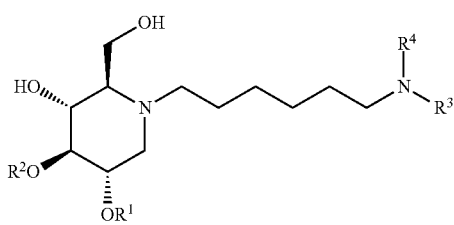

wherein:
R$^1$ and R$^2$ are independently selected from hydrogen and COR$^5$; and when R$^1$ is hydrogen, R$^2$ is not hydrogen;

R$^3$ is selected from hydrogen, optionally substituted C$_{1-6}$ alkyl, optionally substituted C$_{3-14}$ cycloalkyl, COR$^6$, CO$_2$R$^7$, SO$_2$R$^8$, CONHR$^9$, and P(O)(OR$^{10}$)$_2$;

R$^4$ is selected from hydrogen, optionally substituted C$_{1-6}$ alkyl, optionally substituted C$_{3-14}$ cycloalkyl, 1-adamantyl, 2-adamantyl, and optionally substituted aryl which may be substituted by 0-5 moieties;

R$^4$ and R$^7$ are taken together with the atom to which they are bound to form an optionally substituted ring having 5 ring atoms;

R$^4$ and R$^7$ are taken together with the atom to which they are bound to form

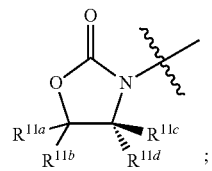

or
R$^4$ and R$^7$ are taken together with the atom to which they are bound to form

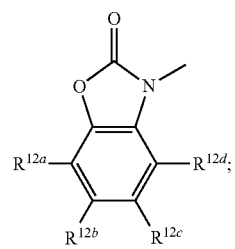

R$^5$ is independently selected from optionally substituted C$_{3-14}$ cycloalkyl, optionally substituted aryl which may be substituted by 0-5 moieties, OR$^{13}$,

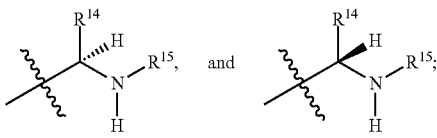

R$^6$ is selected from optionally substituted C$_{1-10}$ alkyl, optionally substituted branched C$_{1-10}$ alkyl, optionally substituted C$_{3-14}$ cycloalkyl, and optionally substituted aryl which may be substituted by 0-5 moieties;

R$^7$ is selected from optionally substituted C$_{1-10}$ alkyl, optionally substituted C$_{3-14}$ cycloalkyl, and optionally substituted branched C$_{1-6}$ alkyl;

R$^8$ is selected from optionally substituted C$_{1-10}$ alkyl, optionally substituted branched C$_{1-10}$ alkyl, optionally substituted C$_{3-14}$ cycloalkyl, and optionally substituted aryl which may be substituted by 0-5 moieties;

R$^9$ is selected from hydrogen, optionally substituted C$_{1-10}$ alkyl, optionally substituted branched C$_{1-10}$ alkyl, optionally substituted C$_{3-14}$ cycloalkyl, and optionally substituted aryl which may be substituted by 0-5 moieties;

R$^{10}$ is selected from optionally substituted C$_{1-10}$ alkyl, optionally substituted branched C$_{3-10}$, and optionally substituted cyclic C$_{3-14}$ cycloalkyl;

R$^{11a}$, R$^{11b}$, R$^{11c}$, and R$^{11d}$ are each independently selected from hydrogen, optionally substituted C$_{1-6}$ alkyl, and optionally substituted aryl which may be substituted by 0-5 moieties;

R$^{12a}$, R$^{12b}$, R$^{12c}$, and R$^{12d}$ are each independently selected from hydrogen, halogen, optionally substituted C$_{1-6}$ alkyl, optionally substituted branched C$_{1-6}$ alkyl, and optionally substituted C$_{1-6}$ alkoxy;

R$^{13}$ is independently selected at each occurrence from a group consisting of optionally substituted C$_{1-10}$ alkyl, optionally substituted branched C$_{1-10}$ alkyl, optionally substituted C3-8 cycloalkyl, and optionally substituted aryl which may be substituted by 0-5 moieties;

R$^{14}$ is selected from a group consisting of optionally substituted C$_{1-10}$ alkyl, optionally substituted branched C$_{1-10}$ alkyl, optionally substituted C$_{3-14}$ cycloalkyl, optionally substituted aryl which may be substituted by 0-5 moieties, optionally substituted benzyl which may be substituted by 0-5 moieties, —CH$_2$OR$^{16}$, CH(CH$_3$)OR$^{16}$, CH$_2$SR$^{16}$, CH$_2$CH$_2$SCH$_3$, CH$_2$CH$_2$CH$_2$CH$_2$NR$^{17a}$R$^{17b}$, CH$_2$COR$^{18}$, CH$_2$CH$_2$COR$^{18}$,

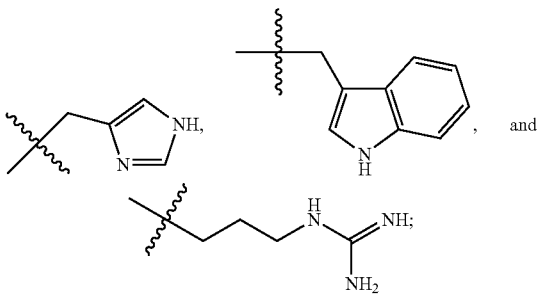

R$^{15}$ is selected from a group consisting of COR$^6$, CO$_2$R$^7$, SO$_2$R$^8$, CONHR$^9$, and P(O)(OR$^{10}$)$_2$;

R$^{16}$ is selected from the group consisting of hydrogen, optionally substituted C$_{1-10}$ alkyl, and optionally substituted branched C$_{1-10}$ alkyl;

R$^{17a}$ is selected from the group consisting of hydrogen, optionally substituted C$_{1-10}$ alkyl, and optionally substituted branched C$_{1-10}$ alkyl;

R$^{17b}$ is selected from the group consisting of hydrogen, optionally substituted C$_{1-10}$ alkyl, and optionally substituted branched C$_{1-10}$ alkyl; and R$^{18}$ is selected from the group consisting of OH, NH$_2$, and C$_{1-6}$ alkoxy; and a hydrate, a solvate, a pharmaceutically acceptable salt, or a complex thereof.

2. The compound according to claim 1, wherein R$^1$ is COR$^5$.

3. The compound according to claim 1, wherein R$^2$ is COR$^5$.

4. The compound according to claim 1, wherein R$^1$ and R$^2$ are COR$^5$.

5. The compound according to claim 4, wherein R$^5$ is OR$^{13}$.

6. The compound according to claim 5, wherein R$^3$ is CONHR$^9$.

7. The compound according to claim 6, wherein R$^4$ is optionally substituted C$_{3-6}$ cycloalkyl.

8. The compound according to claim 7, wherein R$^9$ is optionally substituted branched C$_{3-6}$ alkyl.

9. The compound according to claim 1, wherein R$^5$ is selected from: OR$^{13}$;

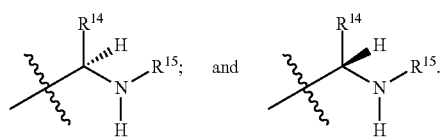

10. The compound according to claim 9, wherein R$^{13}$ is selected from: optionally substituted C$_{1-10}$ alkyl, optionally substituted branched C$_{1-10}$ alkyl, optionally substituted C$_{3-8}$ cycloalkyl, and optionally substituted aryl which may be substituted by 0-5 moieties.

11. The compound according to claim 1, wherein R$^3$ is selected from: optionally substituted C$_{1-6}$ alkyl, optionally substituted C$_{3-14}$ cycloalkyl, COR$^6$, CO$_2$R$^7$, and CONHR$^9$.

12. The compound according to claim 1, wherein R$^3$ is selected from: optionally substituted C$_{1-6}$ alkyl, optionally substituted C$_{3-8}$ cycloalkyl, and CONHR$^9$.

13. The compound according to claim 1, wherein R$^4$ is selected from: optionally substituted C$_{1-6}$ alkyl, optionally substituted C$_{3-14}$ cycloalkyl, and optionally substituted aryl which may be substituted by 0-5 moieties.

14. The compound according to claim 1, wherein R$^9$ is selected from: hydrogen, optionally substituted C$_{1-10}$ alkyl, optionally substituted branched C$_{1-10}$ alkyl, and optionally substituted C3-14 cycloalkyl.

15. A compound according to claim 1, having the formula XXVIII(b):

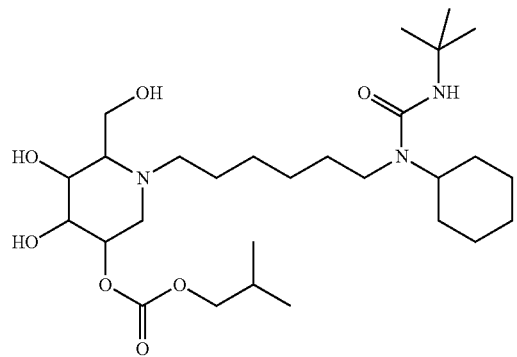

XXVIII(b)

or a pharmaceutically acceptable salt thereof.

16. A compound according to claim 1, having the formula XXX(a):

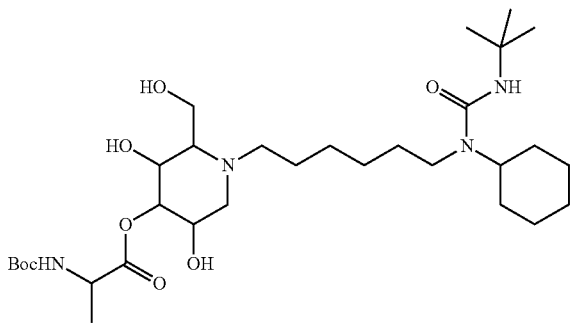

XXX(a)

or a pharmaceutically acceptable salt thereof.

17. A composition comprising a compound according to claim 1, and a pharmaceutically acceptable carrier.

18. A method for treating a disease or condition associated with a virus selected from an arenavirus, a filovirus, a bunyavirus, and a flavivirus, wherein the disease or condition is selected from: Bovine viral diarrhea virus (BVDV); Dengue virus (DENV); Yellow fever virus (YFV); Ebola virus (EBoV); Marburg virus (MARV); Lassa fever virus (LFV); Tacaribe virus (TARV); and Rift Valley fever virus (RVFV), said method comprising administering to a subject in need thereof, an effective amount of a compound according to claim 1.

19. A compound of formula XXVII(a):

XXVII(a)

[chemical structure]

or a pharmaceutically acceptable salt thereof.

20. A compound of formula XXVIII(a):

XXVIII(a)

[chemical structure]

or a pharmaceutically acceptable salt thereof.

* * * * *